(12) United States Patent
Chi Sing et al.

(10) Patent No.: US 8,636,635 B2
(45) Date of Patent: Jan. 28, 2014

(54) BRACHYTHERAPY APPARATUS, SYSTEMS, AND METHODS FOR USING THEM

(75) Inventors: Eduardo Chi Sing, Dana Point, CA (US); Tommy G. Nguyen, Irvine, CA (US)

(73) Assignee: Cianna Medical, Inc., Aliso Viejo, CA (US)

(*) Notice: Subject to any disclaimer, the term of this patent is extended or adjusted under 35 U.S.C. 154(b) by 511 days.

(21) Appl. No.: 12/543,469

(22) Filed: Aug. 18, 2009

(65) Prior Publication Data

US 2010/0048978 A1 Feb. 25, 2010

Related U.S. Application Data

(60) Provisional application No. 61/089,855, filed on Aug. 18, 2008.

(51) Int. Cl.
*A61N 5/00* (2006.01)
*A61M 36/00* (2006.01)

(52) U.S. Cl.
USPC ............ 600/1; 600/6; 600/7; 600/15; 600/19; 600/41; 604/915; 604/912; 606/198; 606/41; 606/46

(58) Field of Classification Search
USPC .................... 600/1–15, 19–41; 604/915, 912; 606/198, 41.46, 41, 46
See application file for complete search history.

(56) References Cited

U.S. PATENT DOCUMENTS

| | | | |
|---|---|---|---|
| 3,060,924 A | 10/1962 | Rush | |
| 3,750,653 A | 8/1973 | Simon | |
| 3,968,803 A | 7/1976 | Hyman | |
| 4,166,469 A * | 9/1979 | Littleford | 607/122 |
| 4,427,005 A | 1/1984 | Tener | |
| 4,580,561 A | 4/1986 | Williamson | |
| 4,706,652 A | 11/1987 | Horowitz | |
| 4,714,074 A | 12/1987 | Rey et al. | |
| 4,798,212 A | 1/1989 | Arana | |
| 4,936,823 A | 6/1990 | Colvin et al. | |
| 4,957,476 A | 9/1990 | Cano | |
| 4,976,680 A | 12/1990 | Hayman et al. | |

(Continued)

FOREIGN PATENT DOCUMENTS

| | | |
|---|---|---|
| DE | 3921291 | 1/1991 |
| DE | 3924291 | 1/1991 |

(Continued)

*Primary Examiner* — Christine Matthews
*Assistant Examiner* — Sunita Reddy
(74) *Attorney, Agent, or Firm* — William A. English; Vista IP Law Group LLP

(57) ABSTRACT

An applicator for delivering brachytherapy includes elongate members movable between collapsed and expanded configurations for delivering brachytherapy within a lumpectomy cavity, a vaginal cavity, or other target region. The elongate members may be expandable into a symmetrical or asymmetrical expanded configuration, e.g., into a generally spherical, pear-shaped, or planar configuration. A system for delivering brachytherapy includes the applicator and an access device for lining and/or dilating a body cavity and/or for receiving the applicator therein. The access device is advanced into a body cavity, an expandable member on the access device is inflated, the applicator is advanced into the access device, and the elongate members are expanded to deliver radiation to the target region. Alternatively, the access device carries an expandable device into the target region, the expandable device is removed after dilating the target region, and the applicator is introduced through the access device to deliver radiation.

34 Claims, 28 Drawing Sheets

(56) References Cited

U.S. PATENT DOCUMENTS

| | | | |
|---|---|---|---|
| 5,056,523 | A | 10/1991 | Hotchkiss, Jr. et al. |
| 5,106,360 | A | 4/1992 | Ishiwara et al. |
| 5,152,741 | A | 10/1992 | Farnio |
| 5,235,966 | A | 8/1993 | Jamner |
| 5,242,372 | A | 9/1993 | Carol |
| 5,279,565 | A | 1/1994 | Klein et al. |
| 5,302,168 | A | 4/1994 | Hess |
| 5,336,178 | A | 8/1994 | Kaplan et al. |
| 5,354,257 | A | 10/1994 | Roubin et al. |
| 5,372,584 | A * | 12/1994 | Zink et al. .................... 604/515 |
| 5,411,466 | A | 5/1995 | Hess |
| 5,423,747 | A | 6/1995 | Amano |
| 5,429,605 | A | 7/1995 | Richling et al. |
| 5,484,384 | A | 1/1996 | Fearnot |
| 5,503,613 | A | 4/1996 | Weinberger |
| 5,509,900 | A | 4/1996 | Kirkman |
| 5,538,502 | A | 7/1996 | Johnstone |
| 5,540,659 | A | 7/1996 | Teirstein |
| 5,611,767 | A | 3/1997 | Williams |
| 5,653,683 | A | 8/1997 | D' Andrea |
| 5,678,572 | A | 10/1997 | Shaw et al. |
| 5,707,332 | A | 1/1998 | Weinberger |
| 5,713,828 | A | 2/1998 | Coniglione |
| 5,720,717 | A | 2/1998 | D' Andrea |
| 5,730,698 | A | 3/1998 | Fischell et al. |
| 5,782,740 | A | 7/1998 | Schneiderman |
| 5,840,008 | A | 11/1998 | Klein et al. |
| 5,843,163 | A | 12/1998 | Wall |
| 5,851,171 | A | 12/1998 | Gasson |
| 5,863,284 | A | 1/1999 | Klein |
| 5,882,291 | A | 3/1999 | Bradshaw et al. |
| 5,891,091 | A | 4/1999 | Teirstein |
| 5,910,102 | A | 6/1999 | Hastings |
| 5,913,813 | A | 6/1999 | Williams et al. |
| 5,916,143 | A | 6/1999 | Apple et al. |
| 5,931,774 | A | 8/1999 | Williams et al. |
| 5,938,582 | A | 8/1999 | Ciamacco, Jr. et al. |
| 5,942,209 | A | 8/1999 | Leavitt et al. |
| 5,976,106 | A | 11/1999 | Verin et al. |
| 6,013,019 | A | 1/2000 | Fischell et al. |
| 6,022,308 | A | 2/2000 | Williams |
| 6,030,333 | A | 2/2000 | Sioshansi et al. |
| 6,033,357 | A | 3/2000 | Ciezki et al. |
| 6,036,632 | A | 3/2000 | Whitmore et al. |
| 6,056,722 | A | 5/2000 | Jayaraman |
| 6,059,752 | A | 5/2000 | Segal |
| 6,071,263 | A | 6/2000 | Kirkman |
| 6,074,339 | A | 6/2000 | Ganbale et al. |
| 6,083,148 | A | 7/2000 | Williams |
| 6,117,064 | A | 9/2000 | Apple et al. |
| 6,159,139 | A | 12/2000 | Chiu |
| 6,159,141 | A | 12/2000 | Apple et al. |
| 6,176,821 | B1 | 1/2001 | Crocker et al. |
| 6,179,766 | B1 | 1/2001 | Dickerson |
| 6,196,996 | B1 | 3/2001 | Teirstein |
| 6,200,256 | B1 | 3/2001 | Weinberger |
| 6,200,257 | B1 | 3/2001 | Winkler |
| 6,213,976 | B1 | 4/2001 | Trerotola |
| 6,217,585 | B1 | 4/2001 | Houser et al. |
| 6,221,003 | B1 | 4/2001 | Sierocuk et al. |
| 6,221,030 | B1 | 4/2001 | Avaltroni |
| 6,234,951 | B1 | 5/2001 | Hastings |
| 6,238,374 | B1 | 5/2001 | Winkler |
| 6,258,099 | B1 | 7/2001 | Mareiro et al. |
| 6,261,320 | B1 | 7/2001 | Tam et al. |
| 6,264,599 | B1 | 7/2001 | Slater et al. |
| 6,264,631 | B1 | 7/2001 | Willis et al. |
| 6,267,775 | B1 | 7/2001 | Clerc et al. |
| 6,287,249 | B1 | 9/2001 | Tam et al. |
| 6,338,709 | B1 | 1/2002 | Geoffrion |
| 6,358,195 | B1 | 3/2002 | Green et al. |
| 6,371,904 | B1 | 4/2002 | Sirimanne et al. |
| 6,413,204 | B1 | 7/2002 | Winkler et al. |
| 6,458,069 | B1 | 10/2002 | Tam et al. |
| 6,482,142 | B1 | 11/2002 | Winkler et al. |
| 6,482,178 | B1 | 11/2002 | Andrews et al. |
| 6,494,824 | B1 | 12/2002 | Apple et al. |
| 6,506,145 | B1 | 1/2003 | Bradshaw et al. |
| 6,508,784 | B1 | 1/2003 | Shu |
| 6,527,692 | B1 | 3/2003 | Weinberger |
| 6,527,693 | B2 | 3/2003 | Munro, III et al. |
| 6,540,656 | B2 | 4/2003 | Fontayne et al. |
| 6,540,734 | B1 | 4/2003 | Chiu et al. |
| 6,554,757 | B1 | 4/2003 | Geitz |
| 6,582,353 | B1 | 6/2003 | Hastings et al. |
| 6,589,158 | B2 | 7/2003 | Winkler |
| 6,592,548 | B2 | 7/2003 | Jayaraman |
| 6,607,476 | B1 | 8/2003 | Barnhart |
| 6,607,478 | B2 | 8/2003 | Williams |
| 6,638,206 | B2 | 10/2003 | Green et al. |
| 6,641,518 | B2 | 11/2003 | Wolfson et al. |
| 6,645,135 | B1 | 11/2003 | Bhat |
| 6,648,811 | B2 | 11/2003 | Sierocuk et al. |
| 6,659,933 | B2 | 12/2003 | Asano |
| 6,673,006 | B2 | 1/2004 | Winkler |
| 6,676,667 | B2 | 1/2004 | Mareiro et al. |
| 6,685,619 | B2 | 2/2004 | Halpern et al. |
| 6,692,460 | B1 | 2/2004 | Jayaraman |
| 6,699,170 | B1 | 3/2004 | Crocker et al. |
| 6,746,465 | B2 | 6/2004 | Diederich et al. |
| 6,752,752 | B2 | 6/2004 | Geitz |
| 6,910,999 | B2 | 6/2005 | Chin et al. |
| 6,923,754 | B2 | 8/2005 | Lubock |
| 6,955,641 | B2 | 10/2005 | Lubock |
| 7,041,047 | B2 | 5/2006 | Gellman et al. |
| 7,056,276 | B2 | 6/2006 | Nakano et al. |
| 7,357,770 | B1 | 4/2008 | Cutrer et al. |
| 2001/0007071 | A1 | 7/2001 | Koblish |
| 2001/0049502 | A1 * | 12/2001 | Chen ..................... 604/167.06 |
| 2002/0016583 | A1 | 2/2002 | Cragg |
| 2002/0032359 | A1 | 3/2002 | Geoffrion et al. |
| 2002/0165427 | A1 | 11/2002 | Yachia et al. |
| 2003/0092957 | A1 | 5/2003 | Scott et al. |
| 2003/0114878 | A1 | 6/2003 | Diederich et al. |
| 2003/0158515 | A1 | 8/2003 | Gonzalez et al. |
| 2003/0163017 | A1 | 8/2003 | Tam et al. |
| 2003/0236443 | A1 | 12/2003 | Cespedes et al. |
| 2004/0006305 | A1 | 1/2004 | Hebert et al. |
| 2004/0068231 | A1 | 4/2004 | Blondeau |
| 2004/0087828 | A1 | 5/2004 | Green et al. |
| 2004/0116767 | A1 | 6/2004 | Lebovic et al. |
| 2004/0127765 | A1 | 7/2004 | Seiler et al. |
| 2004/0260142 | A1 | 12/2004 | Lovoi |
| 2005/0061533 | A1 | 3/2005 | Lovoi |
| 2005/0075662 | A1 | 4/2005 | Pederson et al. |
| 2005/0080313 | A1 | 4/2005 | Stewart et al. |
| 2005/0090845 | A1 | 4/2005 | Boyd |
| 2005/0096647 | A1 | 5/2005 | Steinke et al. |
| 2005/0101823 | A1 | 5/2005 | Linares et al. |
| 2005/0101860 | A1 | 5/2005 | Patrick et al. |
| 2005/0124843 | A1 | 6/2005 | Singh |
| 2005/0182286 | A1 | 8/2005 | Lubock |
| 2005/0240074 | A1 | 10/2005 | Lubock |
| 2006/0015166 | A1 | 1/2006 | Kindlein et al. |
| 2006/0020156 | A1 | 1/2006 | Shukla |
| 2006/0094923 | A1 | 5/2006 | Mate |
| 2006/0100475 | A1 * | 5/2006 | White et al. ..................... 600/3 |
| 2006/0116546 | A1 | 6/2006 | Eng |
| 2006/0173233 | A1 | 8/2006 | Lovoi |
| 2006/0173235 | A1 | 8/2006 | Lim et al. |
| 2006/0184192 | A1 | 8/2006 | Markworth et al. |
| 2006/0199990 | A1 | 9/2006 | Rioux et al. |
| 2006/0200188 | A1 * | 9/2006 | Nance et al. ................. 606/198 |
| 2006/0235365 | A1 | 10/2006 | Terwilliger et al. |
| 2006/0258895 | A1 | 11/2006 | Maschke |
| 2007/0106108 | A1 * | 5/2007 | Hermann et al. ................. 600/7 |
| 2007/0167664 | A1 | 7/2007 | Hermann et al. |
| 2007/0167665 | A1 | 7/2007 | Hermann |
| 2007/0167667 | A1 | 7/2007 | Lubock et al. |
| 2007/0191668 | A1 | 8/2007 | Lubock et al. |
| 2007/0270627 | A1 * | 11/2007 | Cutrer et al. ..................... 600/7 |
| 2008/0091055 | A1 | 4/2008 | Nguyen |
| 2008/0221384 | A1 | 9/2008 | Chi Sing |

(56) References Cited

U.S. PATENT DOCUMENTS

| | | |
|---|---|---|
| 2009/0043327 A1 | 2/2009 | Delsman |
| 2009/0156882 A1 | 6/2009 | Chi Sing |
| 2009/0209802 A1* | 8/2009 | Francescatti et al. ............ 600/3 |

FOREIGN PATENT DOCUMENTS

| | | |
|---|---|---|
| EP | 0318447 B1 | 9/1994 |
| EP | 0390528 B1 | 1/1997 |
| EP | 0775505 | 5/1997 |
| EP | 0536888 B1 | 1/1998 |
| EP | 0906769 | 4/1999 |
| EP | 0955071 | 11/1999 |
| EP | 0884977 B1 | 4/2003 |
| EP | 0782410 B1 | 12/2003 |
| EP | 0955071 | 2/2004 |
| EP | 1402922 | 3/2004 |
| EP | 1405600 | 4/2004 |
| EP | 0808129 B1 | 5/2004 |
| EP | 1428477 | 6/2004 |
| EP | 1568397 | 8/2005 |
| WO | 00/59378 | 10/2000 |
| WO | 01/95808 | 12/2001 |
| WO | 03/077768 | 9/2003 |
| WO | 03/079907 | 10/2003 |
| WO | 2005037363 | 4/2005 |

* cited by examiner

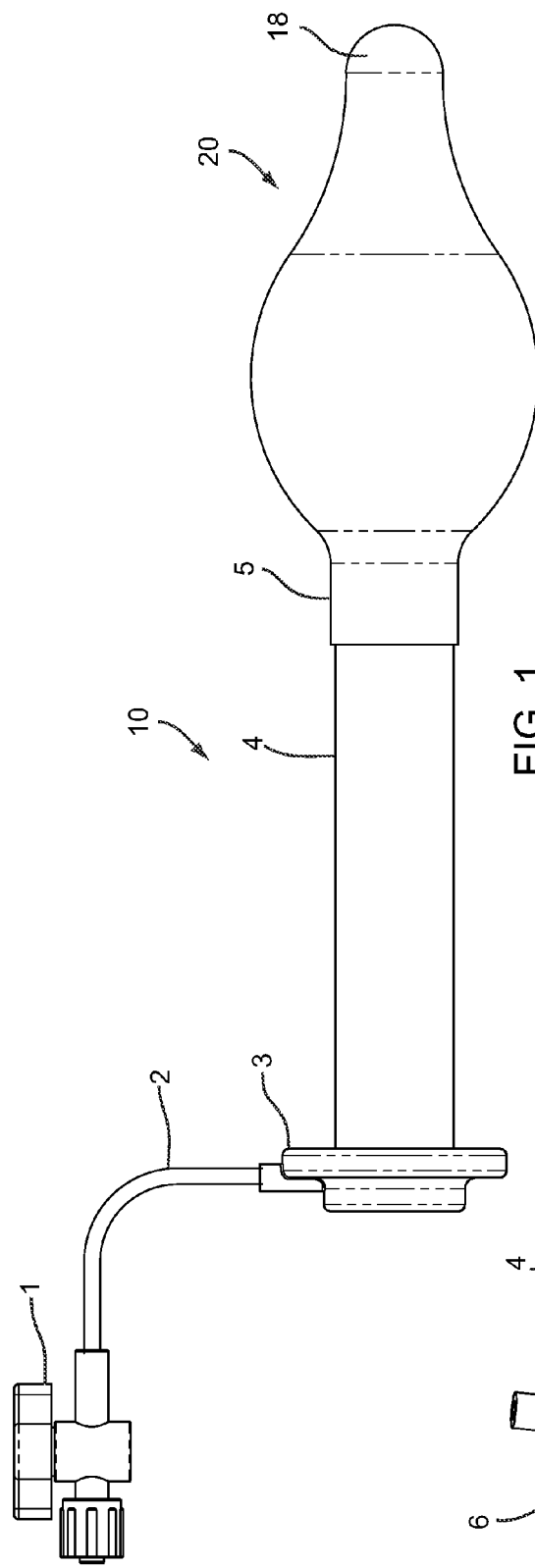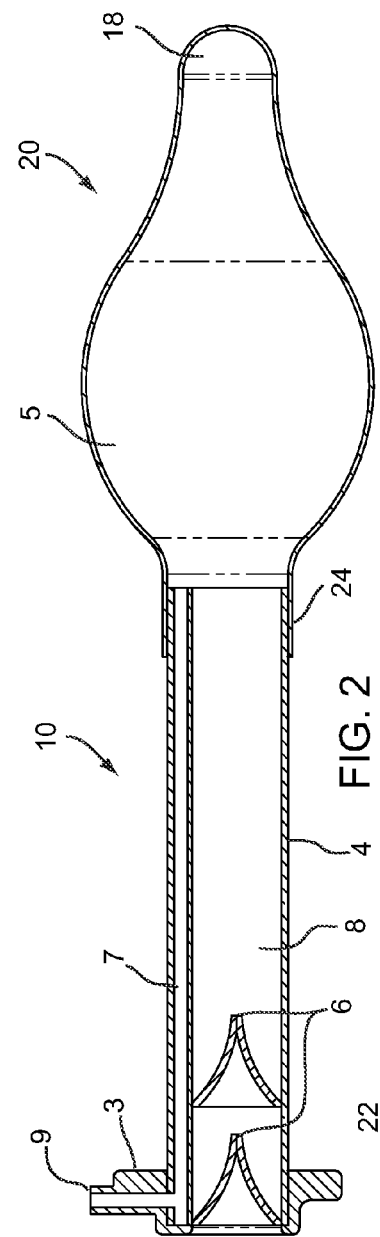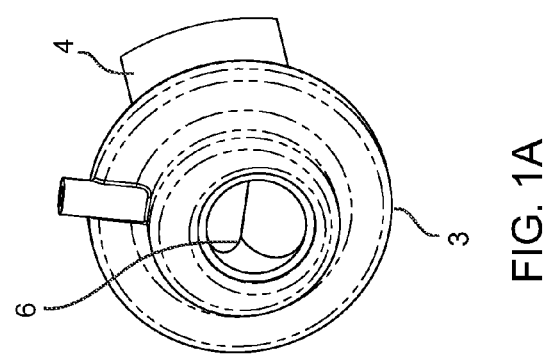

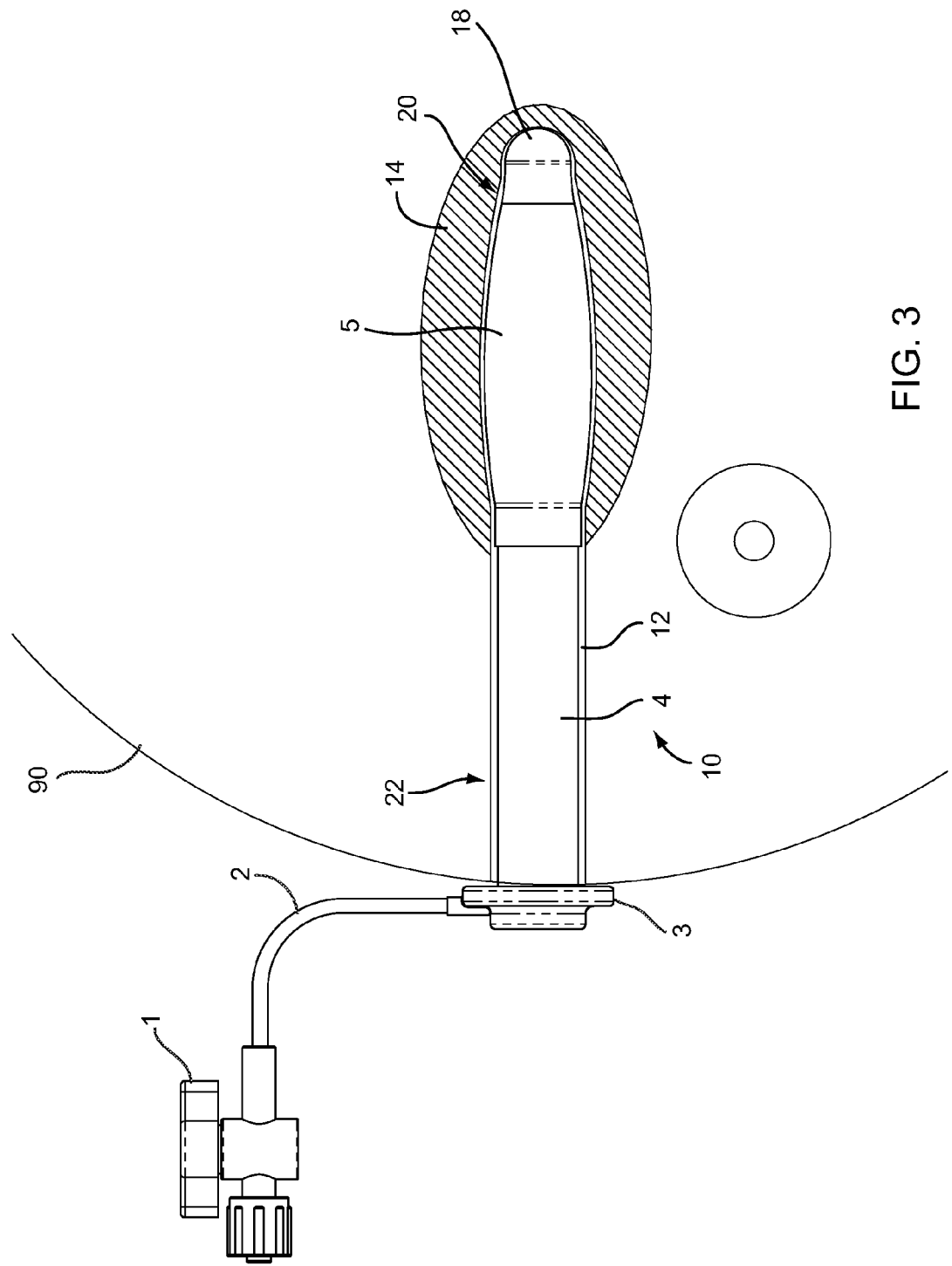

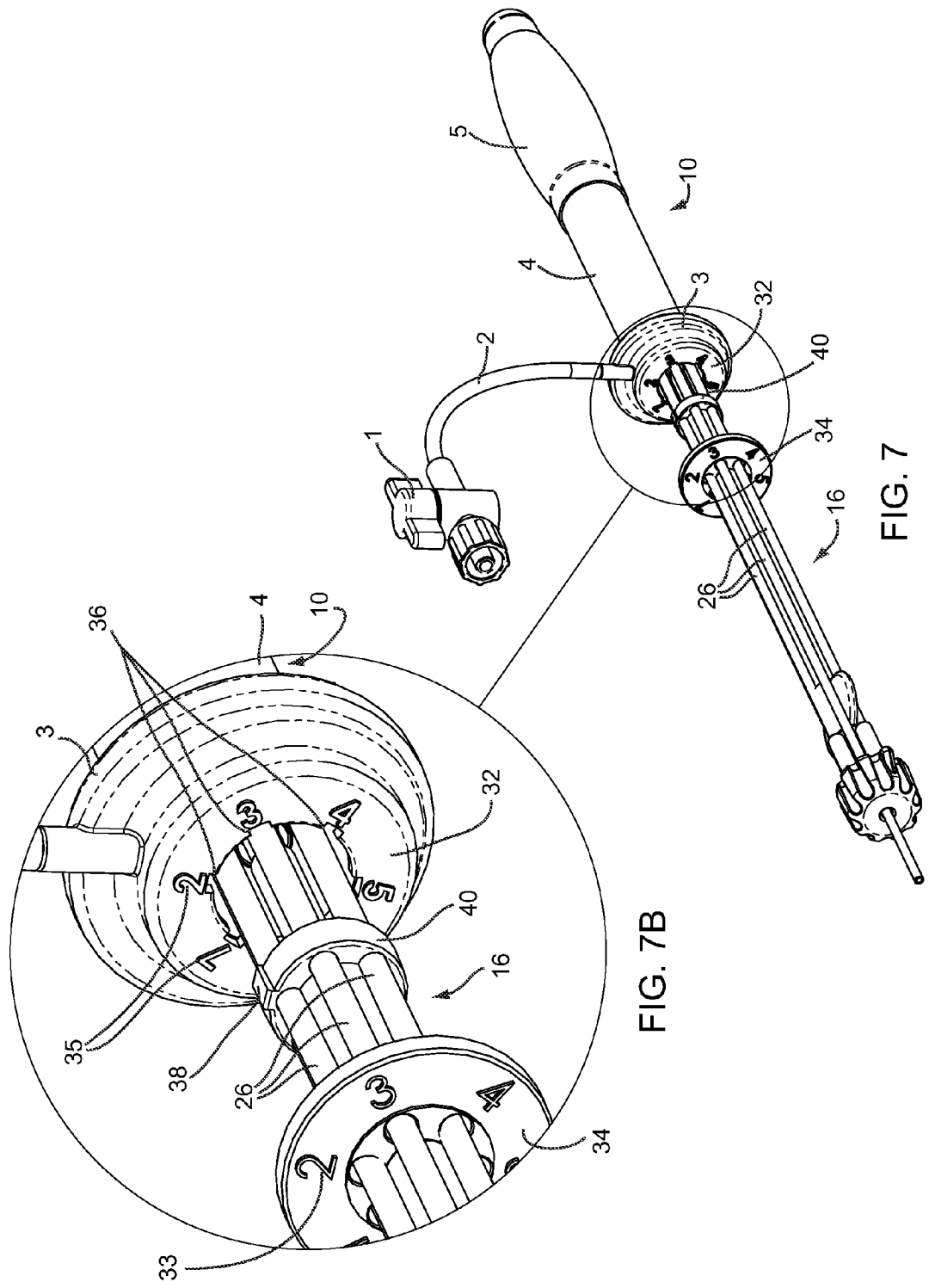

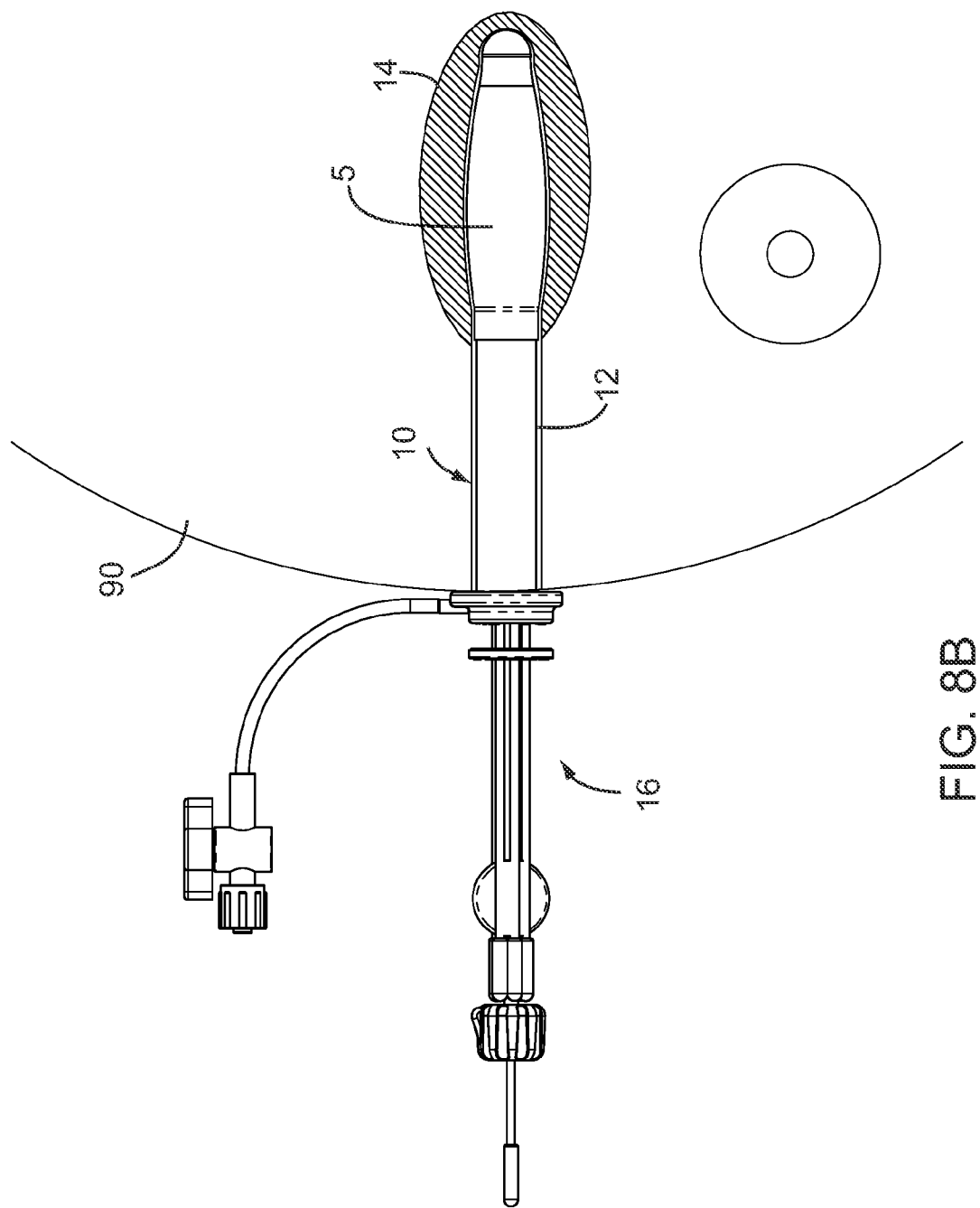

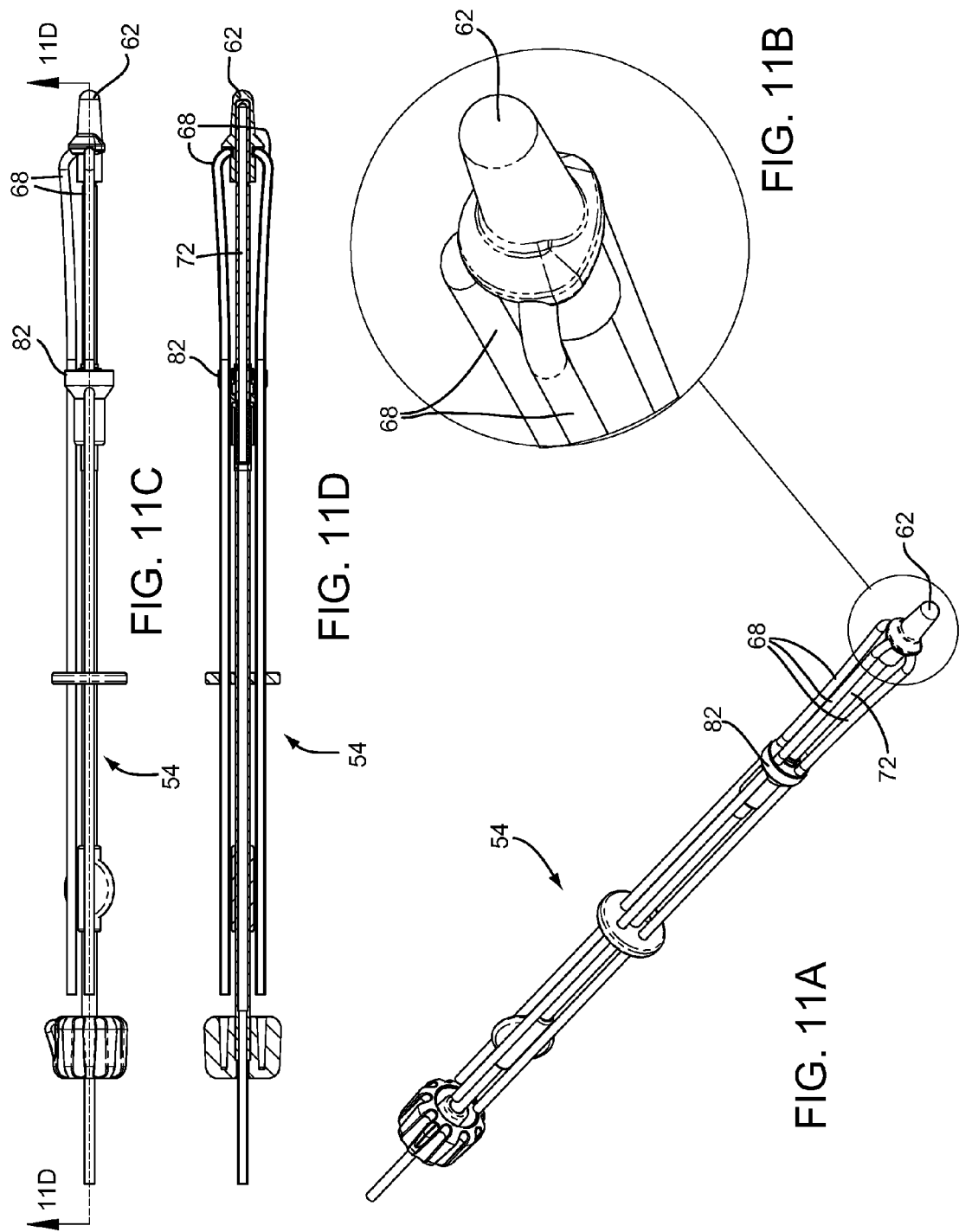

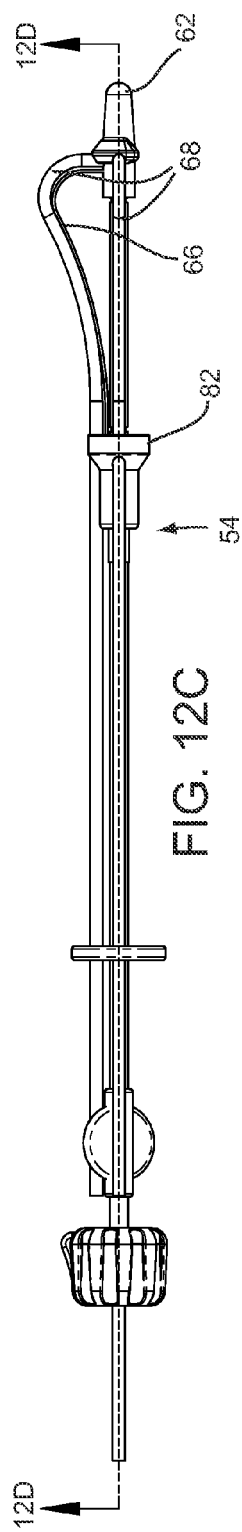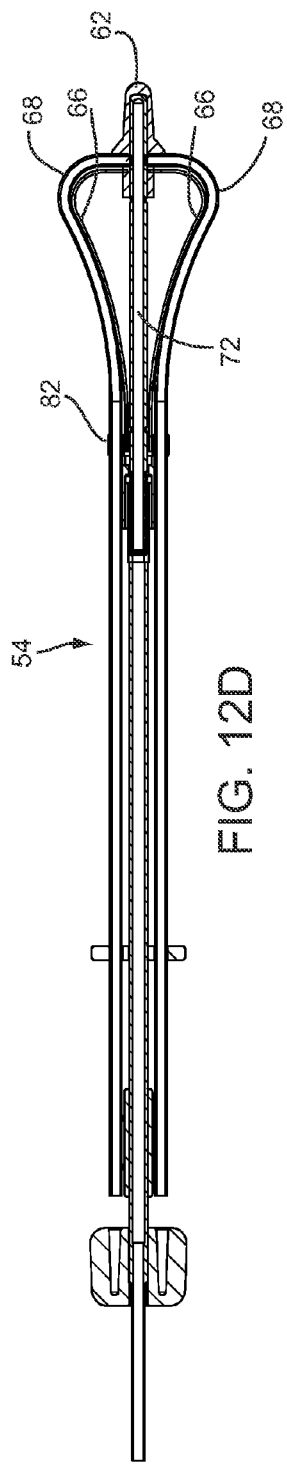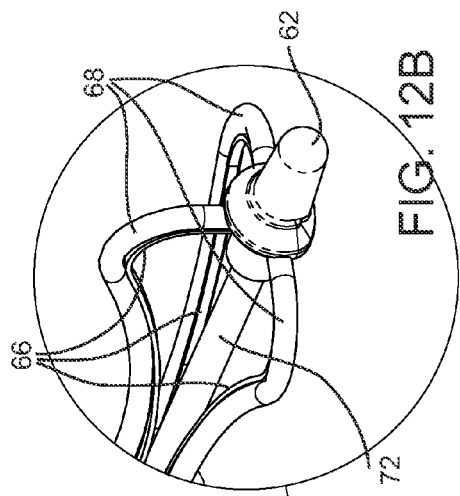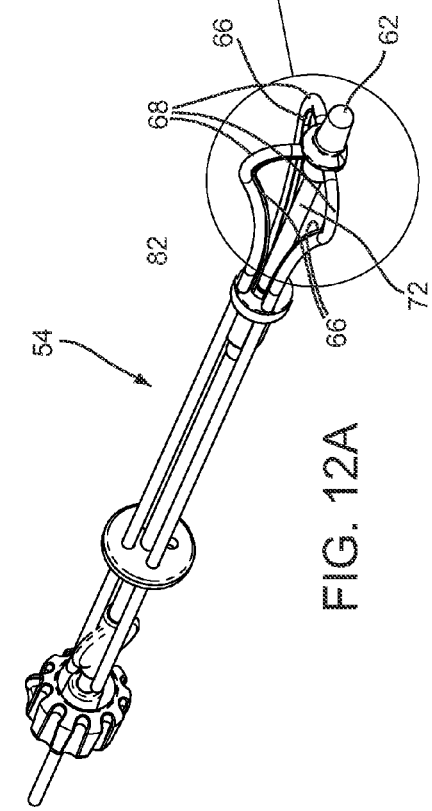

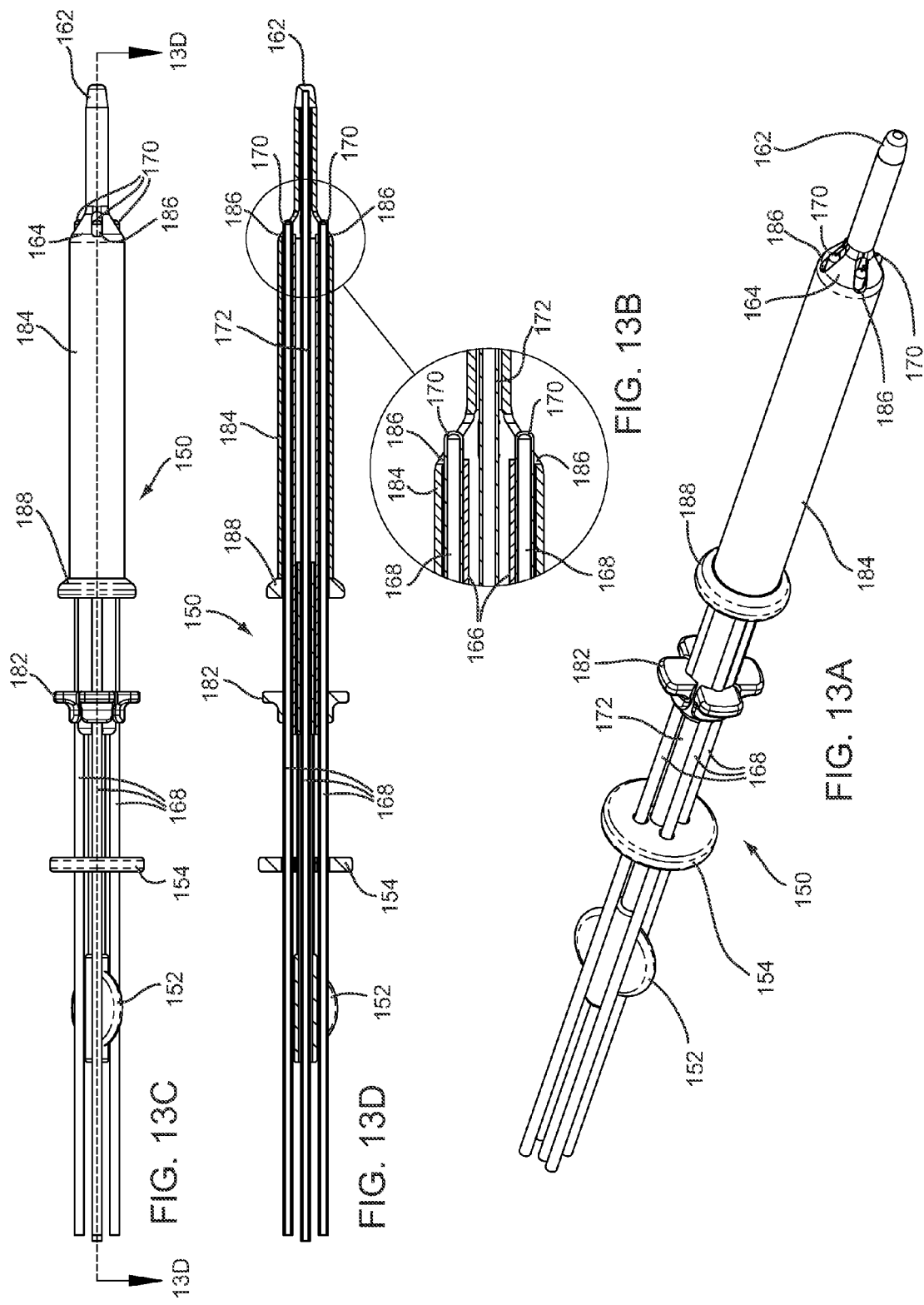

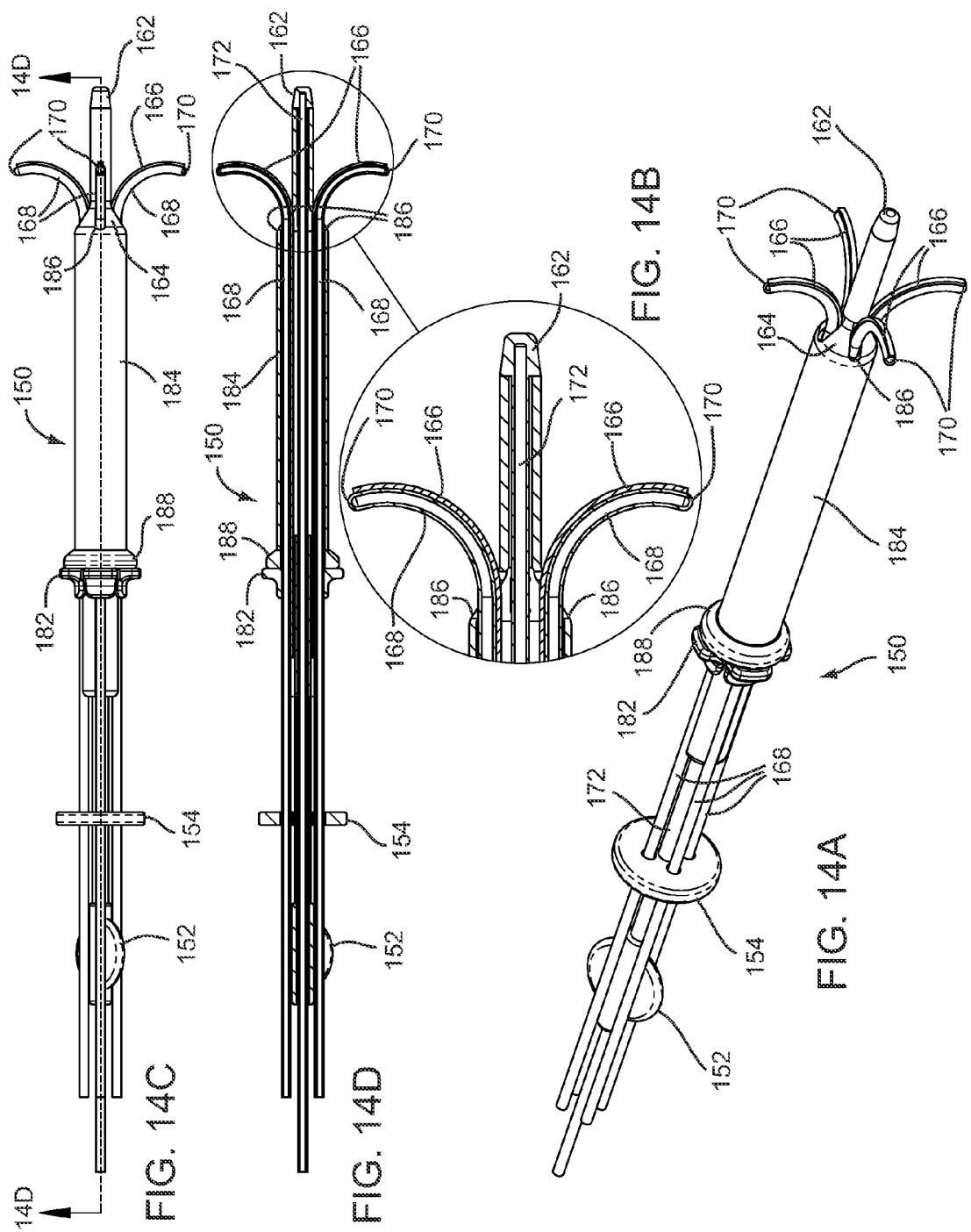

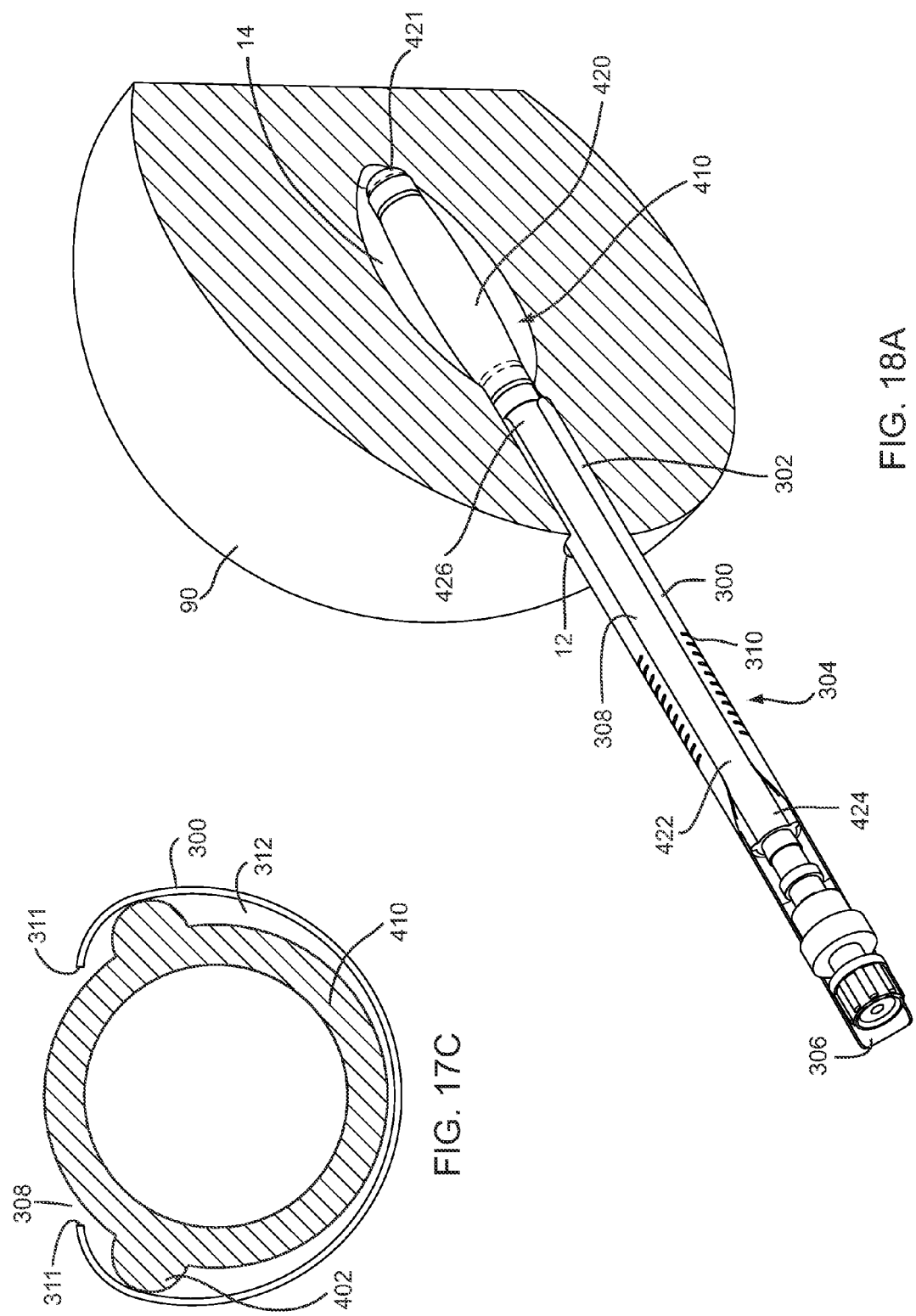

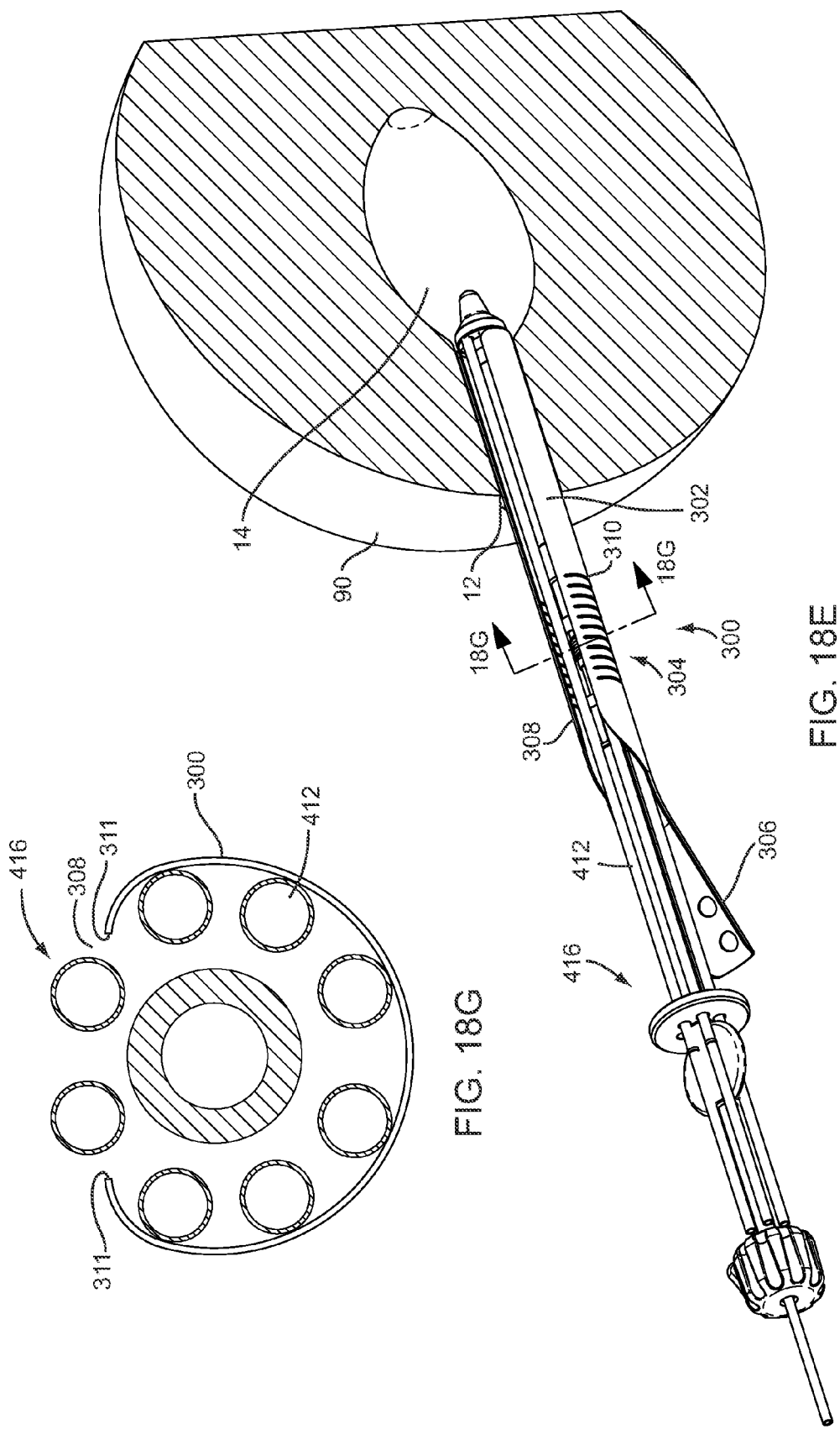

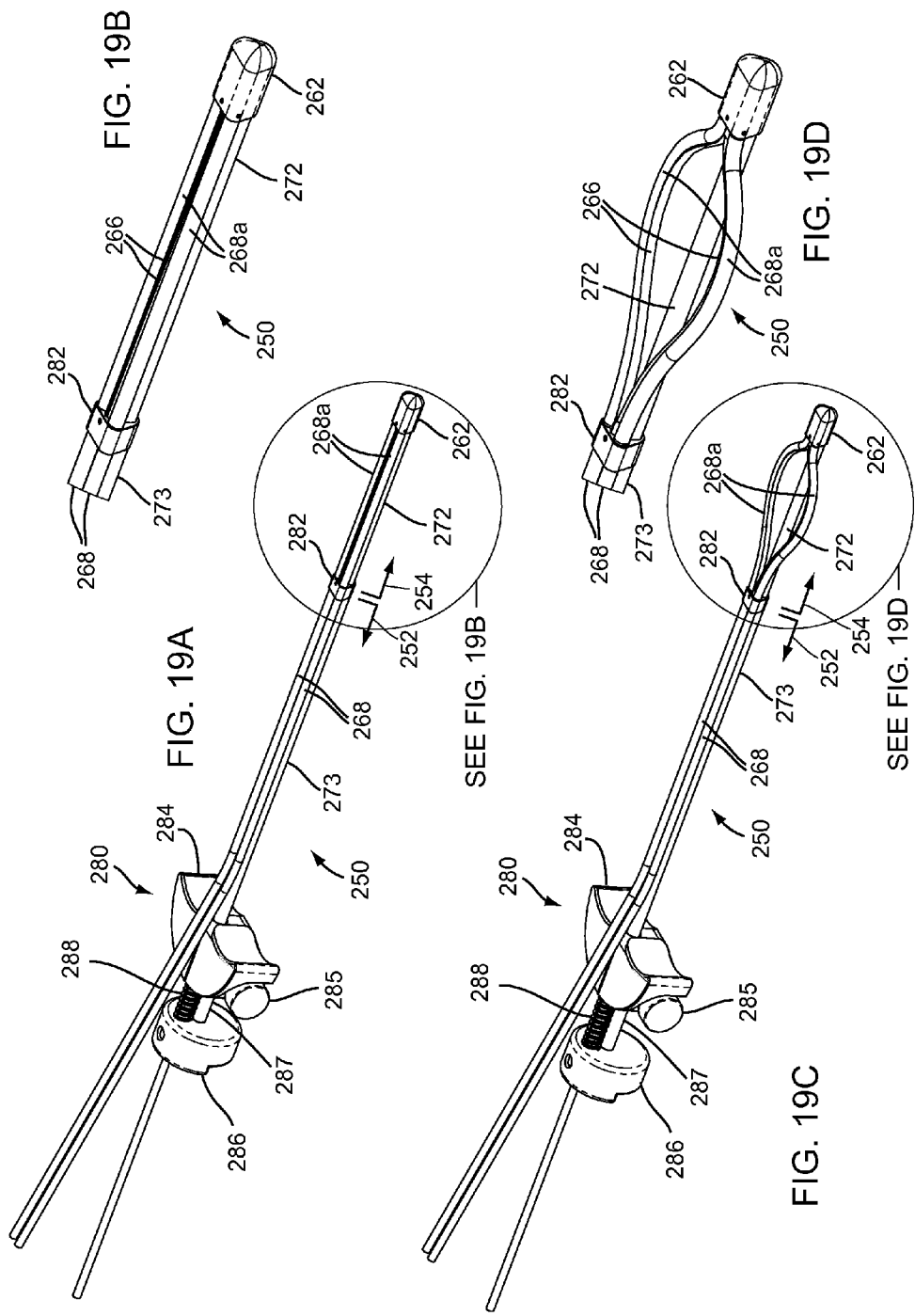

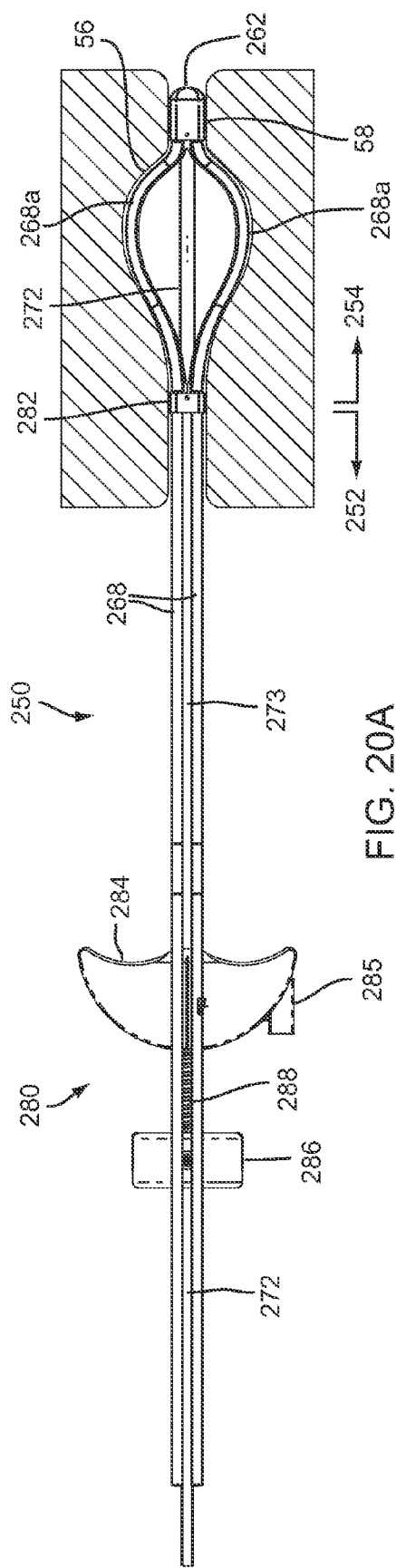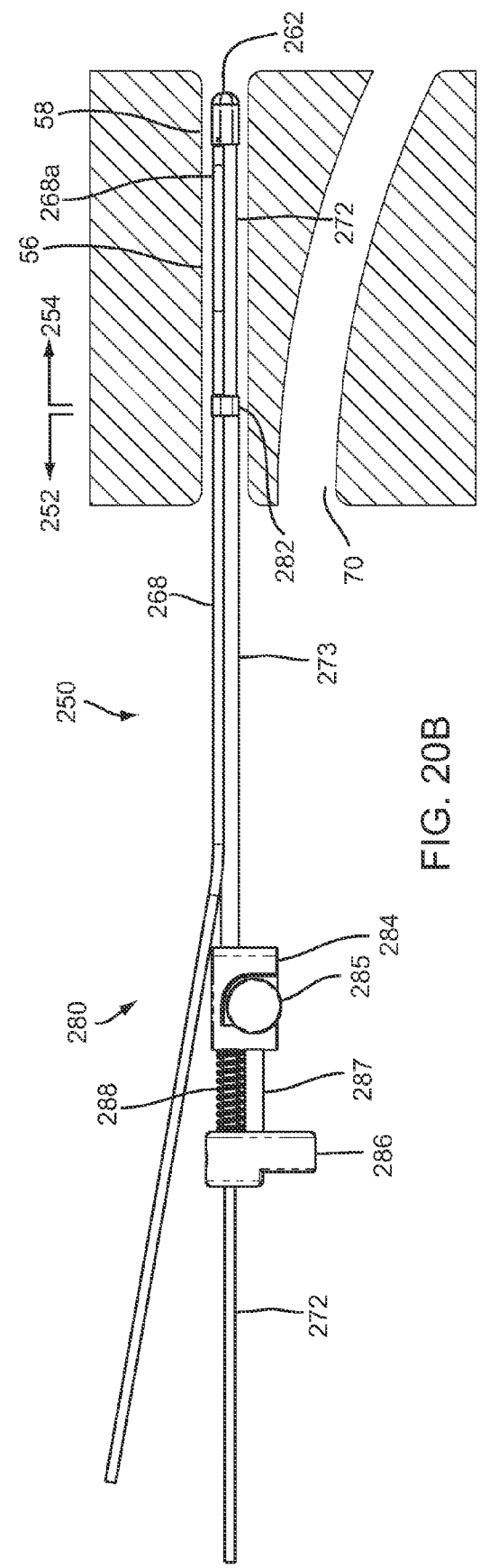

BRACHYTHERAPY APPARATUS, SYSTEMS, AND METHODS FOR USING THEM

RELATED APPLICATION DATA

This application claims benefit of provisional application Ser. No. 61/089,855, filed Aug. 18, 2008, the entire disclosure of which is expressly incorporated by reference herein.

FIELD OF THE INVENTION

The present invention relates generally to apparatus, systems, and methods for providing brachytherapy to a human or other mammalian body, and more particularly to expandable apparatus for performing brachytherapy treatment within tissue, e.g., within breast tissue and/or within a body cavity, e.g., within a lumpectomy cavity or vaginal cavity, and to methods for performing brachytherapy using such apparatus.

BACKGROUND

Brachytherapy is a type of radiation therapy used to treat malignant tumors, such as cancer of the breast or prostate. In general, brachytherapy involves positioning a radiation source directly into target tissue, which may include a tumor and/or tissue surrounding a cavity or void, which may contain potentially cancerous cells (such as a cavity or void created by removing a tumor).

Brachytherapy is often divided into two categories: high dose rate (HDR) and low dose rate (LDR) brachytherapy. In HDR brachytherapy, a high activity radiation source is placed into target tissue, often via a previously implanted catheter, for a short period of time, e.g., lasting from several seconds to a few minutes. In contrast, LDR brachytherapy involves placing a low activity radiation source into the target tissue for a longer, sometimes indefinite, period of time.

Both forms of brachytherapy have advantages. For instance, HDR brachytherapy provides higher radiation levels delivered over a shorter dose delivery period. LDR brachytherapy, on the other hand, utilizes lower activity radiation sources. The energy field of the LDR radiation source results in a measured and localized dose of radiation delivered to target tissue, e.g., a tumor, gland, or other tissue surrounding a cavity or void. However, the energy field thereafter decays to avoid excessive exposure of nearby healthy tissue.

Due in part to the lower activity of LDR radiation sources, LDR brachytherapy may provide various advantages. For example, for healthcare workers, exposure precautions for LDR brachytherapy may be less stringent than those for HDR brachytherapy. Also, there are radiobiological advantages of LDR brachytherapy over HDR brachytherapy (e.g., the dose rate effect), which may lead to better sparing of normal tissue during treatment. Moreover, for patients, the relatively longer implantation period associated with LDR brachytherapy may result in fewer visits to a healthcare facility over the course of radiation treatment, as compared to HDR brachytherapy where patients must return to the healthcare facility for each fraction of radiation delivered, which, for breast brachytherapy, may typically include eight to ten (8-10) fractions.

Common radiation sources used in LDR brachytherapy include radioactive isotopes such as Palladium (Pd)-103, Iodine (I)-125, Gold (Au)-198, and Iridium (Ir)-192. While the size and shape of the isotopes may vary, they may be provided in a standardized size of cylindrically shaped capsules that are approximately the size of a grain of rice, e.g., about 0.8 millimeter in diameter and about 4.5 millimeters in length, and are often referred to as "seeds."

LDR seeds are often delivered through needles using a guide template. The guide template may include a matrix of holes that guide the longitudinal advancement of the needles to ensure their proper position relative to the target tissue. Once the needles are properly located in the target tissue, the seeds may be deposited along the longitudinal axis of each needle, after which the needles may be withdrawn.

While effective, current brachytherapy implementations have potential drawbacks. For example, LDR seeds are typically left indwelling and free floating within the target tissue and are, therefore, susceptible to migration. Moreover, once implanted, LDR seeds are generally not considered removable or repositionable. LDR brachytherapy may also require careful dose distribution calculations and seed mapping before, and often during, seed implantation. Such calculation and mapping may allow effective radiation delivery to the target tissue volume, while minimizing radiation to surrounding healthy tissue (e.g., the urethra and rectum, for example, in prostate brachytherapy). Yet, while such dose calculation and seed mapping techniques are effective, problems may exist, such as potentially significant variability in accuracy of seed placement among different clinicians.

Yet another issue with conventional LDR brachytherapy techniques is that they may require the radioactive seeds to be manipulated individually at the time of implantation, which may be a time-consuming process. Moreover, conventional LDR delivery needles are generally limited to delivering the seeds linearly (along a relatively straight line). Thus, to achieve a desired therapy profile, numerous implants (e.g., including about 50-100 seeds, as are common with prostate brachytherapy) are often required, in conjunction with potentially complex dose distribution and mapping techniques and equipment.

SUMMARY

The present invention is generally directed to apparatus, systems, and methods for delivering brachytherapy to a localized target tissue region. While potentially useful in treating most any area of the body, an exemplary application is treating breast tissue, e.g., breast tumors or lumpectomy cavities. For example, the apparatus and systems herein may be used to place and remove a localized radiation source for both neoadjuvant and post-excisional treatment. Another exemplary application is treating cervical and/or uterine tissue, where the apparatus and systems herein may be used to place and remove a localized radiation source in an existing body cavity, e.g., a vaginal cavity.

In accordance with one embodiment, a system is provided for delivering one or more therapeutic elements (e.g., radiation sources) relative to a target tissue region. Once delivered, the radiation sources may be either immediately withdrawn (e.g., in HDR applications), or left in place, e.g., implanted, for a defined period of time (e.g., in LDR applications). In either instance, the radiation sources may deliver therapy to the target tissue region in accordance with a predefined therapy profile.

In some embodiments, an access port device may be introduced into a body cavity adjacent to the target tissue region and left in place between fractions of radiation. The access port device may facilitate insertion and/or removal of therapeutic tools and may have a low profile to minimize patient discomfort.

In other embodiments, a sheath may be introduced into a passage through tissue that leads to a body cavity and left in place between fractions of treatment. The sheath may delineate and/or dilate the passage, maintain access to the body cavity, facilitate insertion and/or removal of therapeutic tools through the passage and into the body cavity, and/or have a low profile to minimize patient discomfort.

As used herein, "radiation source" and "radioactive source" may include any therapeutic element operable to deliver a dose of radiation. For example, the radiation source may be one or more radioactive seeds or, alternatively, one or more LDR or HDR wire elements (e.g., Iridium wire), e.g., as disclosed in the applications incorporated by reference elsewhere herein.

The term "implantable," as used herein, indicates the capability of a device to be inserted into the body and then maintained in a relatively fixed or static position within the surrounding tissue for an extended period of time, e.g., an hour or more and/or several hours or more, including several days or more.

Furthermore, "target tissue," "target tissue region," "target region," and "target tissue volume," as used herein, may include any portion of a human (or other mammalian) body that has been identified to benefit from radiation therapy. For example, the target tissue region may be a tumor or lesion itself, tissue proximate or surrounding the tumor, a cavity region created by tumor excision (such as the surrounding tissue or cavity associated with a lumpectomy cavity of the breast), or a natural body cavity, such as the vaginal cavity.

It should be noted that the apparatus, systems, and methods described herein may be used for LDR or HDR brachytherapy, as described elsewhere herein and in the applications incorporated by reference herein. Moreover, while described herein with respect to brachytherapy, the apparatus, systems, and methods may apply to other therapy regimens that benefit from the removable implantation of therapy-delivering elements. In exemplary applications, the apparatus, systems, and methods are described herein for treating breast cancer, cervical cancer and/or uterine cancer. However, it will be appreciated that the apparatus, systems, and methods described herein may be used for treating other cancers or conditions that may benefit from brachytherapy treatment.

In accordance with one embodiment, a brachytherapy treatment apparatus is provided that includes an elongate core member; a distal tip at a distal end of the core member; an actuator axially moveable relative to the core member, at least one of the actuator and the distal tip movable axially relative to the other of the actuator and the distal tip; and a plurality of expandable elongate members coupled to the actuator and the distal end of the core member. The expandable elongate members are movable from a collapsed configuration extending substantially parallel to the core member, to an expanded configuration when the actuator is directed distally relative to the distal tip. The elongate members include pathways for receiving a source of radiation therealong. For example, the elongate members may be tubular bodies and the pathways may be lumens extending through the tubular bodies.

In an exemplary embodiment, in the expanded configuration, the expandable elongate members may form a pear shape that bulges near the distal end of the core member and tapers towards the actuator. In another exemplary embodiment, the expandable elongate members may define a planar configuration, e.g., including a pair of elongate members that expand away from one another substantially within a plane.

In still another exemplary embodiment, the plurality of expandable elongate members may be arranged asymmetrically around the core member. For example, the plurality of expandable elongate members may be disposed on one side of a plane extending substantially parallel to a longitudinal axis of the core member. More particularly, the apparatus may include two or three expandable elongate members that are disposed substantially on one side of a plane defined by a central longitudinal axis of the core member. The distal tip of the brachytherapy treatment apparatus may be configured for positioning within a cervix, e.g., having a tapered and/or extended tip shape.

Optionally, in any of these embodiments, the apparatus may include a plurality of elongate support members configured for supporting respective expandable elongate members when the elongate members are directed between the collapsed and expanded configurations. For example, the support members may be attached to the plurality of expandable elongate members for biasing the plurality of expandable elongate members to expand generally radially without substantial lateral movement.

In accordance with another embodiment, a brachytherapy treatment apparatus is provided that includes an elongate core member, a distal tip at a distal end of the core member, an actuator axially moveable relative to the core member, the actuator and/or distal tip movable axially relative to one another, and a plurality of elongate members coupled to the actuator and including unattached or free distal ends that are constrained in a collapsed configuration that extends substantially parallel to the core member. The elongate members are movable between the collapsed configuration and an expanded configuration when the actuator is directed distally relative to the distal tip, e.g., such that the distal ends of the elongate members are directed transversely away from the core member. The expandable elongate members include pathways for receiving a source of radiation therealong.

In an exemplary embodiment, in the expanded configuration, the distal ends of the expandable elongate members may curve radially outwardly away from the core member. For example, the support members may be carried by and/or coupled to respective elongate members for expanding the distal ends of the elongate members away from the core member as the distal ends are exposed or otherwise deployed.

Optionally, the apparatus may include a core member handle fixedly attached to the core member. The plurality of elongate members may be fixedly coupled to the actuator while the core member may be slidable within a central opening of the actuator.

In one embodiment, the apparatus may include a sleeve sized for receiving a portion of the elongate members, e.g., at least the distal ends of the elongate members, and a portion of the elongate core member therein. The distal tip of the apparatus may be fixedly coupled to the sleeve. The sleeve may include one or more openings sized for allowing the distal ends of the elongate members to pass therethrough, e.g., a plurality of openings allowing the distal ends to be exposed or otherwise deployed from the sleeve. In the expanded configuration, the actuator may contact a proximal shoulder of the sleeve, thereby limiting further deployment of the distal ends of the elongate members.

In one embodiment, the apparatus may include a plurality of support members configured for supporting respective elongate members, e.g., to bias the elongate members to be deployed in a predetermined orientation when directed to the expanded configuration. For example, the support members may be attached to respective elongate members for biasing the elongate members to curve radially outwardly away from the core member upon deployment.

In accordance with still another embodiment, a device for delineating or dilating tissue surrounding a body cavity is provided that includes a proximal end; a distal end sized for introduction into a body cavity, an expandable member on the distal end for delineating or dilating the tissue surrounding the body cavity, an access port ring on the proximal end, an inflation lumen extending between the proximal end and the expandable member, and a working lumen or channel extending between the proximal end and the expandable member and sized for receiving a therapeutic treatment device therein. Optionally, the device may include a duck bill or other valve in the working lumen for preventing substantial fluid flow out of the working lumen yet accommodating receiving one or more devices therethrough. The device may be configured to have a low profile when positioned within the body cavity and/or to allow the device to remain within the body cavity for extended periods of time, e.g., between fractionations of brachytherapy treatment. In one embodiment, the access port ring may include an index with a plurality of position labels and a respective plurality of grooves associated with the plurality of position labels.

In accordance with yet another embodiment, an access device is provided for delineating or dilating a passage through tissue that leads to a body cavity. The access device may include a sheath including a distal portion sized for introduction into a passage through tissue, a bendable section adjacent the distal section, and a proximal portion, e.g., including a pull tab, handle, or other feature for manipulating the access device. The sheath may include an at least partially enclosed lumen extending between the proximal and distal portions. The bendable section may be configured to curve to define an angle between the proximal and distal portions, e.g., up to ninety degrees (90°) without pinching or catching tissue. The length of the sheath may be such that the distal portion may be disposed through a passage through tissue to access a body cavity or other target tissue region while the bendable section remains outside the patient's body. In exemplary embodiments, the bendable section may be corrugated or may include a plurality of slots or other features to accommodate bending the bendable section.

In accordance with still another embodiment, a method is provided for brachytherapy treatment of tissue that includes introducing a distal end of an access port device into a body cavity, expanding an expandable member on the distal end of the access port device within the cavity, advancing an elongate body carrying a plurality of elongate members through the access port device into the body cavity with the elongate members in a collapsed configuration, directing the elongate members to an expanded configuration within the body cavity to position the elongate members away from a central axis, and delivering radiation to a target location adjacent to the body cavity via the elongate members. In one embodiment, the body cavity is a vaginal cavity and expanding the expandable member dilates the vaginal cavity. In another embodiment, the method further includes creating a tract through tissue to the body cavity.

Optionally, the method may include deflating the expandable member after directing the elongate members to the expanded configuration and before delivering the radiation. The method may further include directing the elongate members to the collapsed configuration, and withdrawing the elongate body from the body cavity. Still further, the method may include advancing a second elongate body carrying a second plurality of elongate members through the access port device into the body cavity with the second plurality of elongate members in a second collapsed configuration, directing the second plurality of elongate members to a second expanded configuration within the body cavity to position the second plurality of elongate members away from the central axis, and delivering a second phase of radiation to the target location adjacent to the body cavity. Still further, the method may include directing the second plurality of elongate members to the second collapsed configuration; and withdrawing the second elongate body from the body cavity. At the end of a course of treatment, the expandable member of the access port device may be deflated, and the access port device may be withdrawn from the body cavity.

In accordance with yet another embodiment, a method is provided for brachytherapy treatment of tissue within a patient's body that includes introducing a distal portion of a sheath into a passage through tissue to access a body cavity or other target tissue region, while a proximal portion of the sheath remains outside the patient's body. Optionally, the sheath may carry an expandable device, e.g., including an elongate shaft and a balloon or other expandable member, that may be introduced with the sheath with the expandable member collapsed. When the expandable member is disposed within the target tissue region, the expandable member may be expanded within the target tissue region, e.g., to dilate tissue surrounding a lumpectomy or other body cavity access using the sheath. Thereafter, the expandable member may be collapsed and the expandable device removed from the sheath, leaving the sheath within the passage to provide further access to the target tissue region.

For example, a distal portion of an applicator may then be introduced through the sheath and into the target tissue region, e.g., for delivering brachytherapy treatment to the target tissue region. In an exemplary embodiment, the distal portion of the applicator may be expanded within target tissue region, and radiation may be deliver to the target tissue region via the applicator. If multiple treatments are needed, the applicator may be removed, leaving the sheath in place. The sheath may include a bendable section that may be bent against the patient's skin to minimize a profile of the sheath while it remains in place. Thus, the sheath may remain within the passage between treatment and, when additional treatment is needed, the bendable section may be bent away from the patient's skin to facilitate introducing an applicator into the target tissue region. After completing any desired treatments, the sheath may be withdrawn from the passage. Alternatively, if only a single treatment is needed, the sheath may be withdrawn after introducing an applicator through the sheath.

In accordance with still another embodiment, a system for brachytherapy treatment of tissue adjacent a cavity within a body is provided that includes an expandable brachytherapy applicator movable from a collapsed configuration to an expanded configuration, and an access port device sized for introduction into a body cavity and for receiving the brachytherapy applicator therein. Optionally, the access port device may include an access port ring with an index and a plurality of grooves. In addition or alternatively, the applicator may also include an indexing bushing and a tab, wherein each of the grooves in the access port device is sized to receive the tab therein. The index may include a plurality of position labels and the indexing bushing may include a plurality of catheter labels, wherein the catheter labels match the position labels.

In one embodiment, the access port device of the system may be configured for insertion into a body cavity and for remaining in the body cavity between phases of treatment. The access port device may include an expandable member on a distal end of a multiple lumen shaft. For example, the access port device may include a proximal end, a distal end sized for introduction into the body cavity, the expandable member on the distal end sized for delineating or dilating the tissue surrounding the body cavity, an access port ring on the proximal end, an inflation lumen extending between the proximal end and the expandable member, and a working lumen or channel extending between the proximal end and the expandable member for receiving the applicator therein.

In one embodiment, the applicator of the system may include an elongate core member, a distal tip at a distal end of the core member, an actuator axially movable relative to the core member, at least one of the actuator and the distal tip movable axially relative to the other of the actuator and the distal tip, and a plurality of expandable elongate members coupled to the actuator. In the collapsed configuration, the expandable members may extend substantially parallel to the core member. In one embodiment, the elongate members may be coupled to the distal end of the core member, and, in the expanded configuration, the expandable elongate members may define a pear shape, e.g., that bulges near the distal end of the core member and tapers towards the actuator. In another embodiment, the elongate members may include unattached or free distal ends, and, in the expanded configuration, the distal ends may be directed transversely away from the core member.

In accordance with yet another embodiment, a system is provided for brachytherapy treatment within a target tissue region of a patient's body accessed via a passage through tissue. The system generally includes a sheath, an expandable device carried by the sheath, and an applicator for delivering radiation or other treatment to the target tissue region. For example, the sheath may include a distal portion sized for introduction into the passage through tissue, a proximal portion, and a bendable section therebetween. The sheath may define an at least partially enclosed lumen extending between the proximal and distal portions The expandable device may include an elongate shaft that may be received in the lumen through the sheath and an expandable member disposed distally beyond the distal portion of the sheath, e.g., for dilating tissue surrounding a body cavity within the target tissue region. The sheath may facilitate introducing the expandable device through the passage into the target tissue region, and the expandable device may be removable from the sheath, e.g., after expanding the expandable member to dilate tissue.

The applicator includes a proximal end, a distal end sized for introduction through the lumen of the sheath, and one or more lumens or other pathways for delivering radiation or other treatment to the target tissue region. For example, the applicator may include a plurality of elongate members extending between the applicator proximal and distal ends that include pathways for receiving a source of radiation for delivering radiation to the target tissue region. The distal end of the applicator may be expandable, e.g., by directing the elongate members from a collapsed configuration to an expanded configuration, to facilitate delivery of radiation according to a desired dose plan.

The above summary is not intended to describe each embodiment or every implementation of the present invention. Rather, a more complete understanding of the invention will become apparent and appreciated by reference to the following detailed description and claims in view of the accompanying drawings.

BRIEF DESCRIPTION OF THE DRAWINGS

FIG. 1 is a side elevation view of an access port device including an expandable member in an expanded configuration.

FIG. 1A is a perspective view of a proximal end of the access port device of FIG. 1.

FIG. 2 is a cross-sectional side view of the access port device of FIG. 1 with the expandable member in the expanded configuration.

FIGS. 3-6 are partial cross-sectional side views of the access port device of FIGS. 1-2, showing a method for brachytherapy treatment of breast tissue that includes using the access port device for introducing a brachytherapy applicator into the breast tissue.

FIGS. 7A and 7B are detailed perspective views of an index that may be provided on the access port device of FIGS. 1-2, and an indexing bushing that may be provided on an applicator being introduced into the access port device.

FIG. 8B is a side view of the apparatus of FIG. 8A showing a method for brachytherapy treatment of breast tissue.

FIG. 11A is a perspective view of the applicator of FIGS. 9A, 9B and 10 in the collapsed configuration.

FIG. 11B is a detailed view of a distal end of the applicator of FIG. 11A.

FIG. 11C is a side elevation view of the applicator of FIG. 11A.

FIG. 11D is a cross-sectional side view of the applicator taken along line 11D-11D in FIG. 11C.

FIG. 12A is a perspective view of the applicator in FIGS. 9A, 9B and 10 in the expanded configuration.

FIG. 12B is a detailed view of the distal end of the applicator of FIG. 12A.

FIG. 12C is a side elevation view of the applicator of FIG. 12A.

FIG. 12D is a cross-sectional side view of the applicator taken along line 12D-12D in FIG. 12C.

FIG. 13A is a perspective view of still another embodiment of an applicator for brachytherapy treatment in a collapsed configuration.

FIG. 13B is a cross-sectional detail of a distal end of the applicator of FIG. 13A.

FIG. 13C is a side elevation view of the applicator of FIG. 13A.

FIG. 13D is a cross-sectional side view of the applicator taken along line 13D-13D in FIG. 13C.

FIG. 14A is a perspective view of the applicator in FIGS. 13A-13D in an expanded configuration.

FIG. 14B is a cross-sectional detail of the distal end of the applicator of FIG. 14A.

FIG. 14C is a side elevation view of the applicator of FIG. 14A.

FIG. 14D is a cross-sectional side view of the applicator taken along line 14D-14D in FIG. 14C.

FIG. 17C is a cross-sectional view of the brachytherapy system of FIG. 17A taken along line 17C-17C.

FIG. 18A is a partial cross-sectional view of a patient's body showing a method for accessing a target tissue region within a breast using the brachytherapy system of FIGS. 17A-17C.

FIGS. 18D and 18E show an applicator being introduced through the access sheath until a distal portion of the applicator is disposed within the target tissue region.

FIG. 18G is a cross-sectional view of the applicator and access sheath of FIG. 18E taken along line 18G-18G.

FIG. 19A is a perspective view of yet another embodiment of an applicator for brachytherapy treatment in a collapsed configuration.

FIG. 19B is a detail of a distal portion of the applicator of FIG. 19A in the collapsed configuration.

FIG. 19C is a perspective view of the applicator of FIG. 19A in an expanded configuration.

FIG. 19D is a detail of the distal portion of the applicator of FIG. 19C in the expanded configuration.

FIGS. 20A and 20B are top and side views, respectively, of the applicator of FIGS. 19A-19D in the expanded configuration and placed against a cervix within a vaginal cavity of a patient's body.

DETAILED DESCRIPTION OF THE EXEMPLARY EMBODIMENTS

Figure 4:
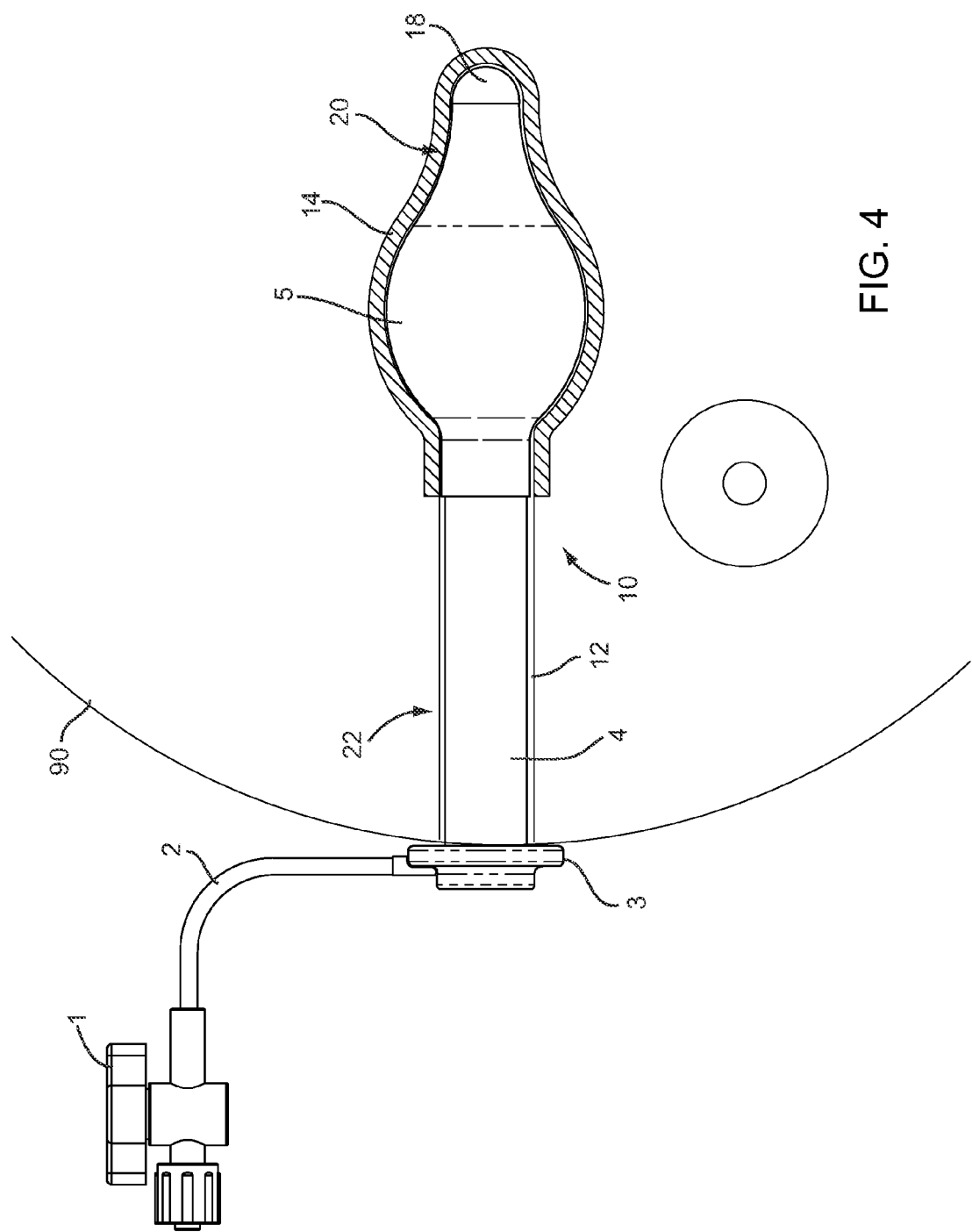

Turning to the drawings, FIGS. 1, 1A, and 2 show an exemplary embodiment of an access port device 10 for expanding, dilating, and/or otherwise lining a body cavity or other target tissue region (not shown), e.g., to facilitate introduction of one or more therapeutic and/or diagnostic instruments (also not shown), e.g., a brachytherapy applicator, into the target tissue region. The access port device 10 generally includes an elongate shaft 4 including a proximal end 22, a distal end 24 sized for introduction through a passage into the body cavity, and an expandable member 5 extending from the distal end 24 to define an expandable distal region 20. The expandable distal region 20 may be in a collapsed configuration while the device 10 is inserted into the body cavity and then may be inflated or otherwise expanded to delineate or dilate the inner wall of the cavity and/or maintain the cavity geometry, e.g., during dosimetry planning.

In an exemplary embodiment, the expandable member 5 may be formed from compliant or semi-compliant material such that, when the expandable member 5 is inflated, e.g., with saline or other inflation media, the expandable member 5 may grow to different volumes with different fill volumes of saline, yet the expandable member 5 material may be sufficiently rigid to provide substantial dilating pressure to the surrounding tissue. The expandable member 5 may include a substantially rigid distal tip 18 to facilitate insertion of the distal region 20 through a tissue tract or other body passage into a body cavity. The size of the expandable member 5 may depend upon the size of the body cavity into which it is to be placed. For example, the expandable member 5 may have a length of between about three to six centimeters (3-6 cm), with the distal tip 18 having a length between about zero and one centimeter (0-1.0 cm), e.g., about seven millimeters (7 mm). In further examples, the expandable member 5 may have a maximum expanded diameter between about three to five centimeters (3-5 cm), a durometer or softness between about 85-95, e.g., about 90 Shore A, and/or a wall thickness of one to two thousandths of an inch (0.025-0.050 mm).

In an exemplary embodiment, the shaft 4 may be a substantially rigid or semi-rigid tubular member, e.g., including an inflation lumen 7 and a working lumen or channel 8. The inflation lumen 7 may extend between the proximal and distal ends 22, 24 of the shaft 4 such that the inflation lumen 7 communicates with an interior of the expandable member 5. As shown, the inflation lumen 7 communicates with a side port 9 on a handle or access port ring 3 to accommodate coupling a source of inflation media and/or vacuum (not shown) to the access port device 10. As shown, flexible tubing 2 extends from the side port 9 to a stopcock 1, which may include a connector, e.g., a Luer lock connector, for connecting a source of inflation media and/or vacuum, e.g., a syringe of saline or other fluid, a vacuum line, and the like to deliver and/or remove inflation media from the interior of the expandable member 5 via the inflation lumen 7.

Figure 5:
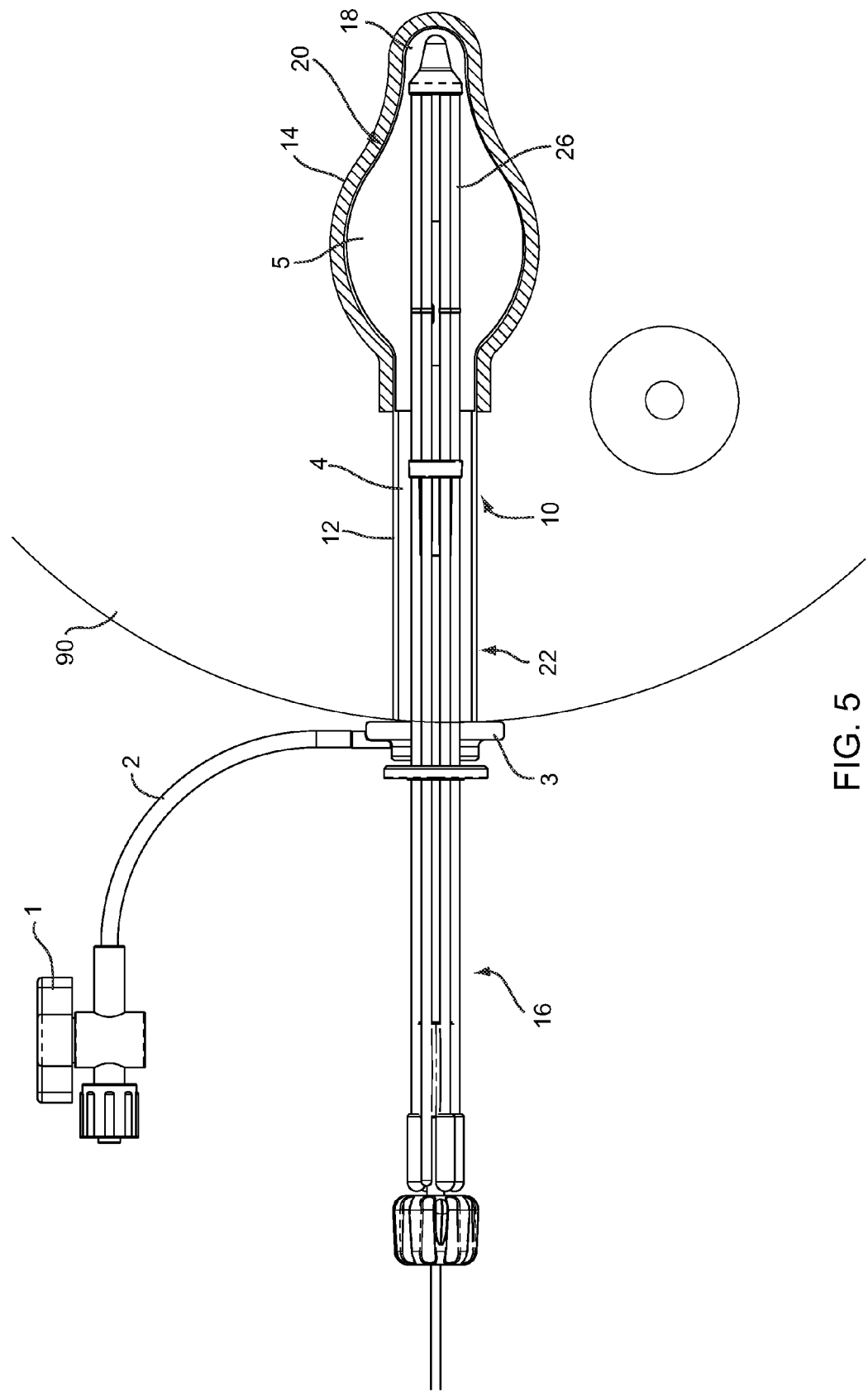
Figure 6:
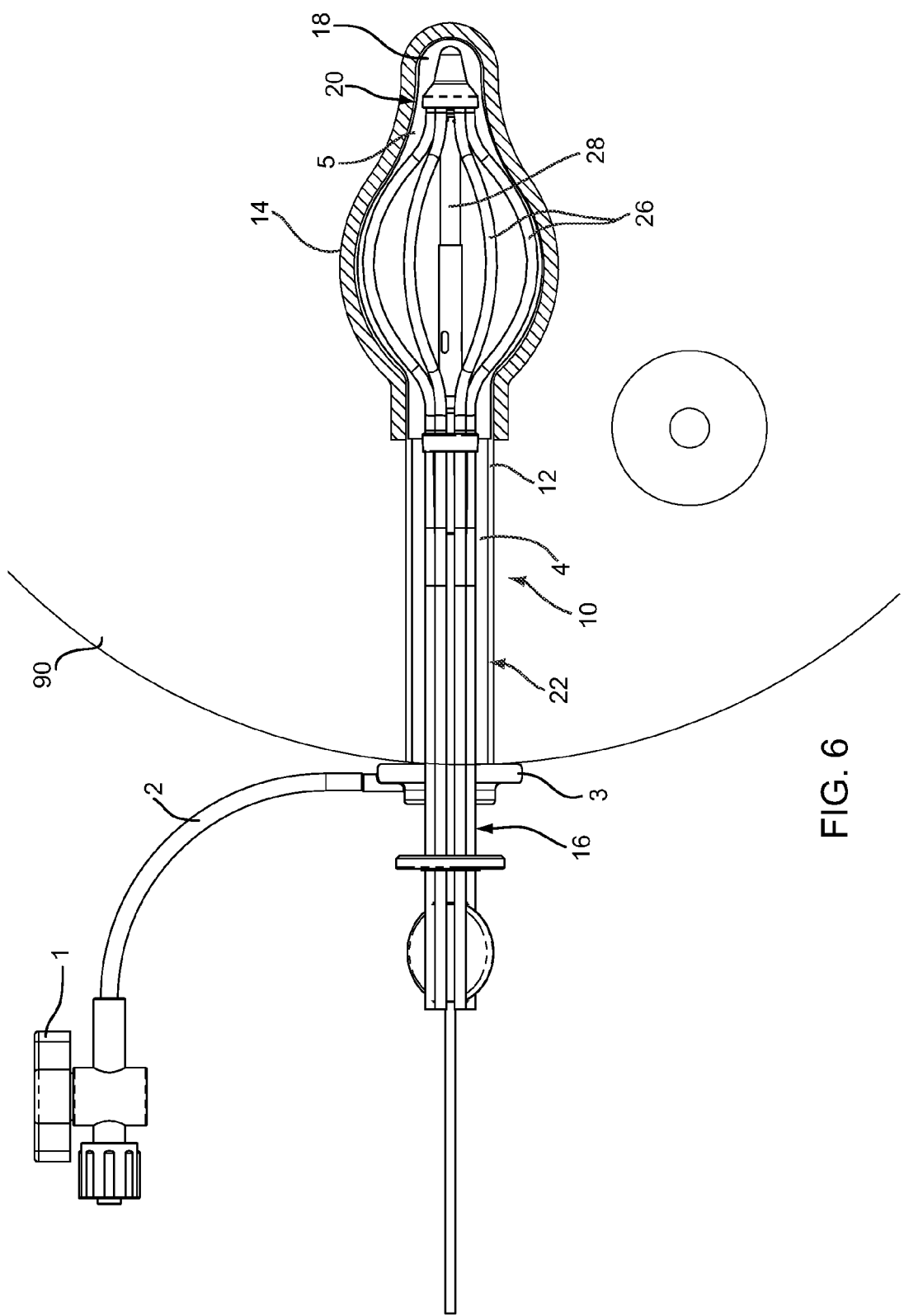

As shown in FIGS. 2, 5, and 6, the working channel 8 may be sized to allow a brachytherapy applicator 16 or other device (not shown) to pass through the shaft 4, e.g., from the proximal end 22 into the interior of the expandable member 5, while preventing substantial fluid flow out of the working channel 8, e.g., to prevent substantial deflation of the expandable member 5. For example, the working channel 8 may include a one-way valve and/or a lubricious inner surface to accommodate receiving one or more devices through the shaft 4 into the expandable member 5. In an exemplary embodiment, best seen in FIG. 2, the working channel 8 may include one or more duck bill valves 6 (two shown adjacent one another) in order to keep the channel 8 substantially sealed during introduction and/or removal of the brachytherapy applicator and/or other devices.

The working channel 8 may be substantially larger than the inflation lumen 7, e.g., such that the working channel 8 can accommodate receiving relatively larger devices therethrough. For example, the working channel 8 may have a diameter or other maximum cross-section between about six and twenty millimeters (6-20 mm), while the inflation lumen 7 may have a diameter or other maximum cross-section between about one and three millimeters (1-3 mm). The working channel 8 and inflation lumen 7 may be coextruded when the shaft 4 is formed, e.g., such that the working channel 8 and inflation lumen 7 are disposed adjacent one another.

The expandable member 5 may be disposed on the distal end 24 of the shaft 4 in communication with the inflation lumen 7 and the working channel 8. The expandable member 5 and the dual lumen shaft 4 may be a single component, or may be formed from separate components that are attached together, e.g., using an interference fit, cooperating connectors, bonding with adhesives, sonic welding, and the like.

The proximal end 22 of the shaft 4 may include an access port ring, handle, or hub 3. The ring 3 may have a diameter sufficiently greater than a diameter of the shaft 4 so that when the distal end 20 of the access port device 10 is inserted through a passage into a body cavity, the ring 3 may remain outside of the body and may prevent the entire access port device 10 from entering the passage. In an exemplary embodiment, the access port ring 3 may have a relatively low profile, e.g., so that it is unobtrusive and patient discomfort is minimized. The overall length of the access port device 10 may be such that, when the expandable member 5 is positioned within a body cavity and the shaft 4 is positioned within a passage through tissue communicating with the body cavity, the ring 3 may remain outside of the patient's body, e.g., such that a surface of the access port ring 3 is in contact with the skin or other outer surface of the patient's body. The shaft 4 and the ring 3 may be a single component, e.g., integrally molded together, or may be formed from separate components that are attached together, e.g., using an interference fit, cooperating connectors, bonding with adhesives, sonic welding, and the like.

In a method for brachytherapy treatment of target tissue surrounding a body cavity or other target tissue region, the access port device 10 may be introduced into the body cavity to facilitate the placement and/or exchange of one or more therapeutic and/or diagnostic instruments or other devices, e.g., an expandable brachytherapy applicator such as those described elsewhere herein and/or in co-pending application Ser. Nos. 10/658,518, filed Sep. 9, 2003 and published as U.S. Publication No. 2004/0116767, 11/276,851, filed Mar. 16, 2006 and published as U.S. Publication No. 2007/0106108, 11/554,731, filed Oct. 31, 2006 and published as U.S. Publication No. 2007/0167664, 11/557,747, filed Nov. 8, 2006 and published as U.S. Publication No. 2007/0167665, 11/757,231, filed Jun. 1, 2007 and published as U.S. Publication No. 2008/0221384, 11/868,483, filed Oct. 6, 2007 and published as U.S. Publication No. 2008/0091055, 61/014,071 filed Dec. 16, 2007, and 11/266,994, filed Nov. 4, 2005 and published as U.S. Publication No. 2006/0100475. The entire disclosures of these applications are expressly incorporated by reference herein.

In an exemplary method, shown in FIGS. 3-6, the access port device 10 may facilitate introduction of an expandable brachytherapy applicator 16 into a cavity 14 within a breast 90. As shown, the breast 90 may have a cavity 14 formed therein, e.g., a lumpectomy cavity created by removing cancerous tissue. With the expandable member 5 in a collapsed configuration, the access port device 10 may be introduced through a tissue tract 12 into the cavity 14, as shown in FIG. 3. The tissue tract 12 may be created in advance, e.g., using a needle or other device (not shown). For example, the tissue tract 12 may be created during the lumpectomy procedure. Alternatively or additionally, the access port device 10 may include a sharp distal tip (not shown) for piercing the tissue, similar to devices disclosed in the applications incorporated by reference elsewhere herein. The access port device 10 may be inserted into the cavity 14 until the distal end 20 of the access port device 10 reaches the distal portion of the cavity 14, the entire expandable member 5 is positioned within the cavity 14, and/or the access port ring 3 is disposed adjacent to or contacts the outer surface of the breast 90. The access port ring 3 may remain on an outer surface of the breast 90 to provide access to the cavity 14 and to facilitate insertion and/or removal of the applicator 16 and/or other devices.

As shown in FIG. 4, the expandable member 5 may then be inflated to contact the walls of the body cavity 14. For example, a syringe or other source of inflation media (not shown) may be coupled to the stopcock 1, which may then be opened to allow delivery of inflation media to inflate the expandable member 5. If desired, the expandable member 5 may be further inflated to dilate the body cavity 14. It will be appreciated that further inflation of the expandable member 5 may result in increased force between the expandable member 5 and the surface of the cavity 14, which may substantially secure and/or otherwise limit undesirable movement of the expandable member 5 within the cavity 14, thereby stabilizing the access port device 10. Once the expandable member 5 is sufficiently inflated, the stopcock 1 may be closed and the source of inflation media may be removed, if desired. At any time, the source of inflation media may be recoupled and the stopcock 1 reopened, if desired to reinflate and/or further expand the expandable member 5 or to collapse the expandable member 5 and remove the access port device 10.

Thereafter, as shown in FIG. 5, the brachytherapy applicator 16 may be inserted into the access port device 10 with the elongate members 26 in their collapsed configuration, e.g., until the distal end of the applicator 16 reaches the distal end 18 of the expandable member 5. The inner surface of the working channel 8 (not shown, see FIG. 2) may include a lubricious coating and/or other material to facilitate axial movement of devices therein, e.g., insertion and/or removal of the applicator 16.

Figure 8A:
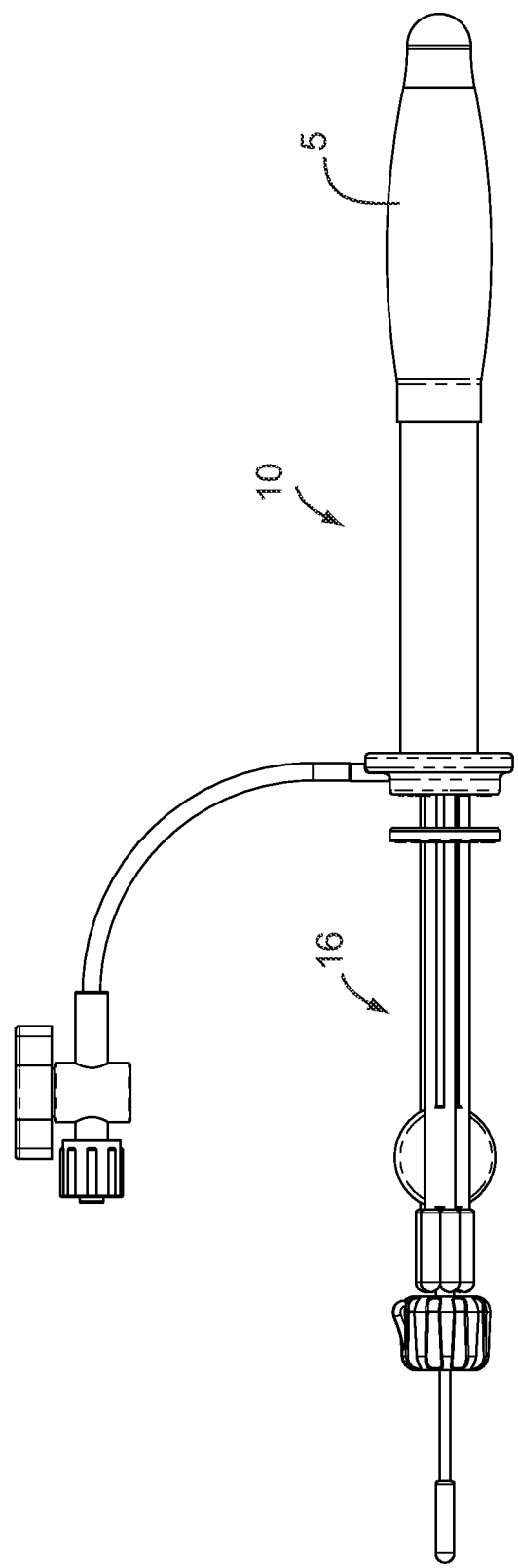
FIG. 8A is a side view of an alternative embodiment of an apparatus for brachytherapy treatment including an access port device and applicator.

Alternatively, rather than being introduced separately, the access port device 10 and the applicator 16 may be coupled together prior to insertion into the cavity 14, as shown in FIG. 8A. With the expandable member 5 and the applicator 16 in collapsed configurations, the applicator 16 may be positioned within the access port device 10, and the access port device 10 and the applicator 16 may then be inserted through the tissue tract 12 into the cavity 14 at the same time, as shown in FIG. 8B. After the simultaneous insertion of the access port device 10 and the applicator 16, the expandable member 5 may be inflated to the desired diameter as discussed above to achieve the configuration shown in FIG. 5.

In an exemplary embodiment, the applicator 16 may include a plurality of catheters, tubular members, or other elongate members 26 with pathways for receiving a source of radiation therealong, as described in greater detail in the applications incorporated by reference elsewhere herein. With the applicator 16 fully inserted into the access port device 10 so that the catheters 26 are within the expandable member 5, the catheters 26 may be expanded to contact the inner surface of the expandable member 5, as shown in FIG. 6. The mechanism and method for expanding the catheters 26 are described in greater detail in the applications incorporated by reference elsewhere herein.

After the catheters 26 are expanded, the expandable member 5 may optionally be deflated, allowing the surrounding tissue to invaginate between the expanded catheters 26, which, as described in the applications incorporated by reference elsewhere herein, may maintain the applicator 16 in place and prevent applicator rotation or axial movement.

Alternatively, the applicator 16 may be expanded without inflating the expandable member 5. With the applicator 16 and the device 10 both in collapsed configurations, the expandable catheters 26 may be expanded without first inflating the expandable member 5. Expansion of the catheters 26 may cause simultaneous expansion of the expandable member 5.

With the device 10 and the applicator 16 in a desired position, one or more radiation sources (not shown) may be directed into lumens of the catheters 26, and/or a center catheter 28 of the applicator 16, e.g., according to a desired dose plan, to deliver radiation to the tissue surrounding the cavity 14. Alternatively or additionally, radiation may be applied while the catheters 26 are in the collapsed configuration. Thus, the catheters 26 and 28 may define pathways for receiving radiation source(s), as described in the applications incorporated by reference elsewhere herein.

After a phase or fractionation of radiation is completed, the catheters 26 may be collapsed, as shown in FIG. 5, and the applicator 16 withdrawn from the cavity 14, as shown in FIG. 4. The access port device 10 may then remain in place, as shown in FIG. 4, e.g., between treatment phases or fractionations of treatment as in the case of brachytherapy treatment. Alternatively, the access port device 10 may remain in place with the expandable member 5 partially deflated or fully deflated as shown in FIG. 3. It will be appreciated that, with the expandable member 5 inflated as shown in FIG. 4, the device 10 may be less likely to shift and more likely to maintain the desired position and cavity geometry. Over several phases of treatment, the applicator 16, and/or other devices, may be inserted and removed several times while the access port device 10 remains substantially in the desired position. Thus, maintaining the access port device 10 in the body cavity may allow the applicator 16 to be easily removed between treatment fractionations and reintroduced (or another applicator, 16 to be introduced) as needed, which may provide for more accurate delivery of a desired dose plan throughout the several phases of treatment. In addition, the access port device 10 may minimize exposure of the applicator 16 to bodily fluids, which may allow the applicator 16 to be easily cleaned, sterilized, and reused, if desired.

After completing a full course of treatment, the expandable member 5 of the access port device 10 may be returned to its collapsed configuration, as shown in FIG. 3 and the access port device 10 removed from the breast 90 via the tissue tract 12. For example, a source of vacuum or aspiration (not shown) may be coupled to the stopcock 1, which may be opened to allow the inflation media to be removed from the interior of the expandable member 5. Alternatively, an open tubular member or other device may simply be inserted through the working channel 8 to open the valves 6 to allow the inflation media within the expandable member 5 to escape freely, thereby collapsing the expandable member 5.

The ability to decouple the access port device 10 and the applicator 16 may allow for compensation of any rotational movement of the access port device 10 between treatment phases by simply re-indexing the applicator 16 back to the original dosimetry planning position.

Turning to FIGS. 7A and 7B, to assist with accurate re-indexing of the applicator 16, the access port ring 3 and the applicator 16 may include an index 32 and an indexing bushing 34, respectively, e.g., for indicating the rotational position of the catheters 26 relative to the surrounding cavity 14. The index 32 may include a plurality of position labels 35 and corresponding grooves 36. The position labels 35 are depicted as numbers, but may alternatively be letters, colors, symbols, and the like. The indexing bushing 34 on the applicator 16 may include a plurality of catheter labels 33 corresponding to the plurality of position labels 35. In an exemplary embodiment, the catheter labels 33 may match the position labels 35. Thus, as shown, the catheter labels 33 are depicted as numbers that match the position labels 35, but may alternatively be letters, colors, symbols, and the like that correspond to the position labels 35.

As best seen in FIG. 7B, the applicator 16 may include a ring 40 adjacent the indexing bushing 34, which includes a tab 38 fixedly attached thereto and sized for insertion into each of the grooves 36. The ring 40 may be fixed to the catheters 26, e.g., to maintain the catheters 26 in their radial positions relative to each other, and the tab 38 may be aligned radially with one of the catheters 26.

By using the catheter labels 33 and the position labels 35 as visual indicators, a clinician may accurately determine the desired rotational position of the applicator 16 relative to the access port device 10 and, thus, to the body cavity 14 (not shown, see FIGS. 3-6), before the applicator 16 is inserted (or reinserted) into the access port device 10, e.g., in order to ensure that the dose plan is accurately followed during a course of treatment. For example, if the access port device 10 rotates between treatment phases, it is possible to easily and accurately determine whether the applicator 16 should be rotated relative to the access port device 10 and into which of the grooves 36 the tab 38 should be inserted in order to maintain the proper orientation of the applicator 16 for the desired dose plan.

For example, if the catheter label 33 marked "2" is originally aligned with the position label 35 marked "2" (as shown), the tab 38 is inserted into the groove 36 corresponding to the position label 35 marked "2" when the applicator 16 is inserted into the access port device 10. The tab 38 and groove 36 prevent rotational movement of the applicator 16 relative to the access port device 10 once the tab 38 is received in the groove 36. In a subsequent treatment phase, if the access port device 10 has rotated counter-clockwise by about 120 degrees, the clinician may easily determine that the tab 38 should be inserted into the groove 36 corresponding to the position label 35 marked "4" in order to compensate for the rotation of the device 10 and apply the same dose plan as was applied in the previous treatment phase.

Figure 9A:
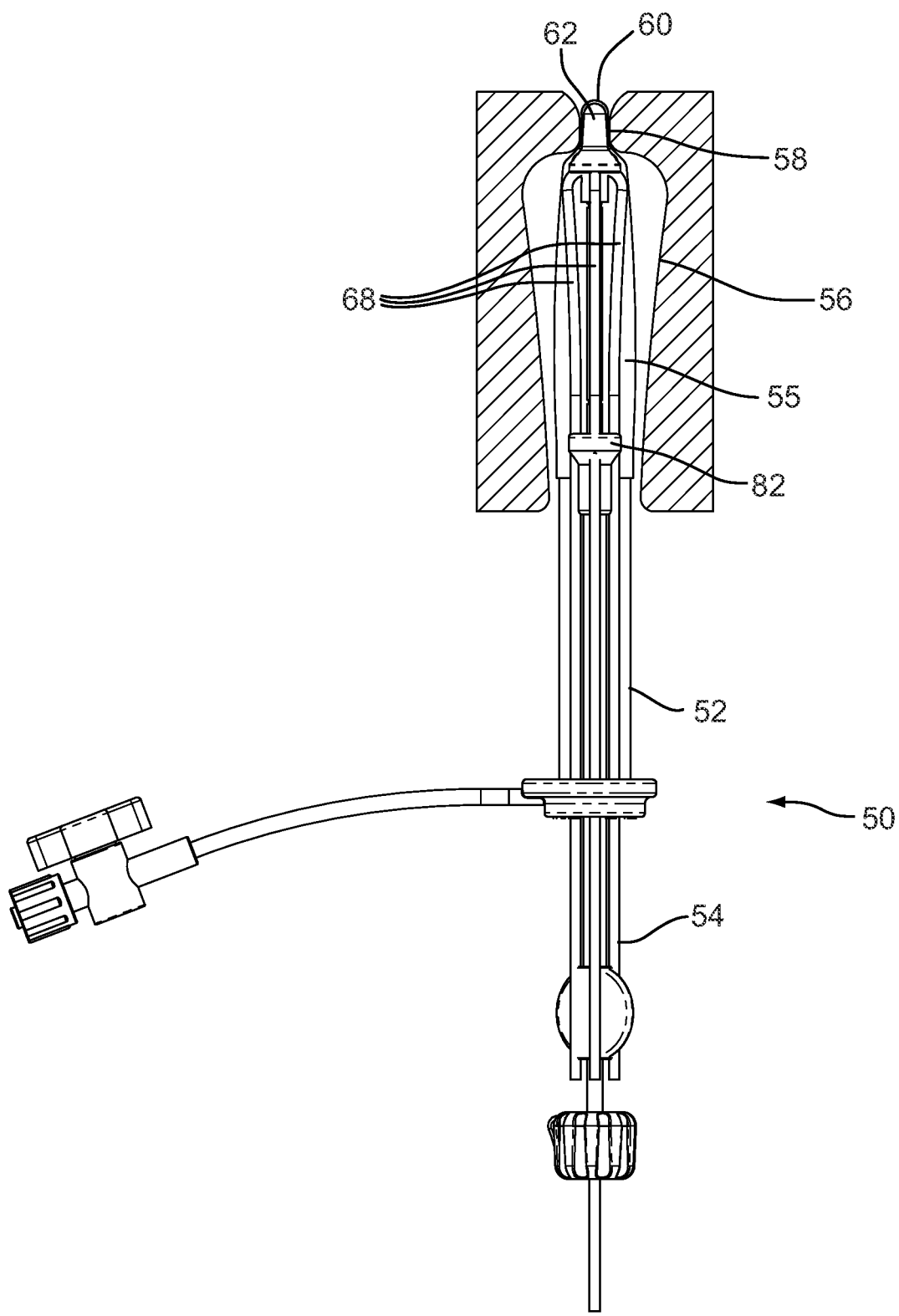
FIGS. 9A and 9B are partial cross-sectional front views of a patient's body showing another embodiment of an access port device and an applicator in a collapsed configuration and an expanded configuration, respectively, introduced within a vaginal cavity.
Figure 9B:
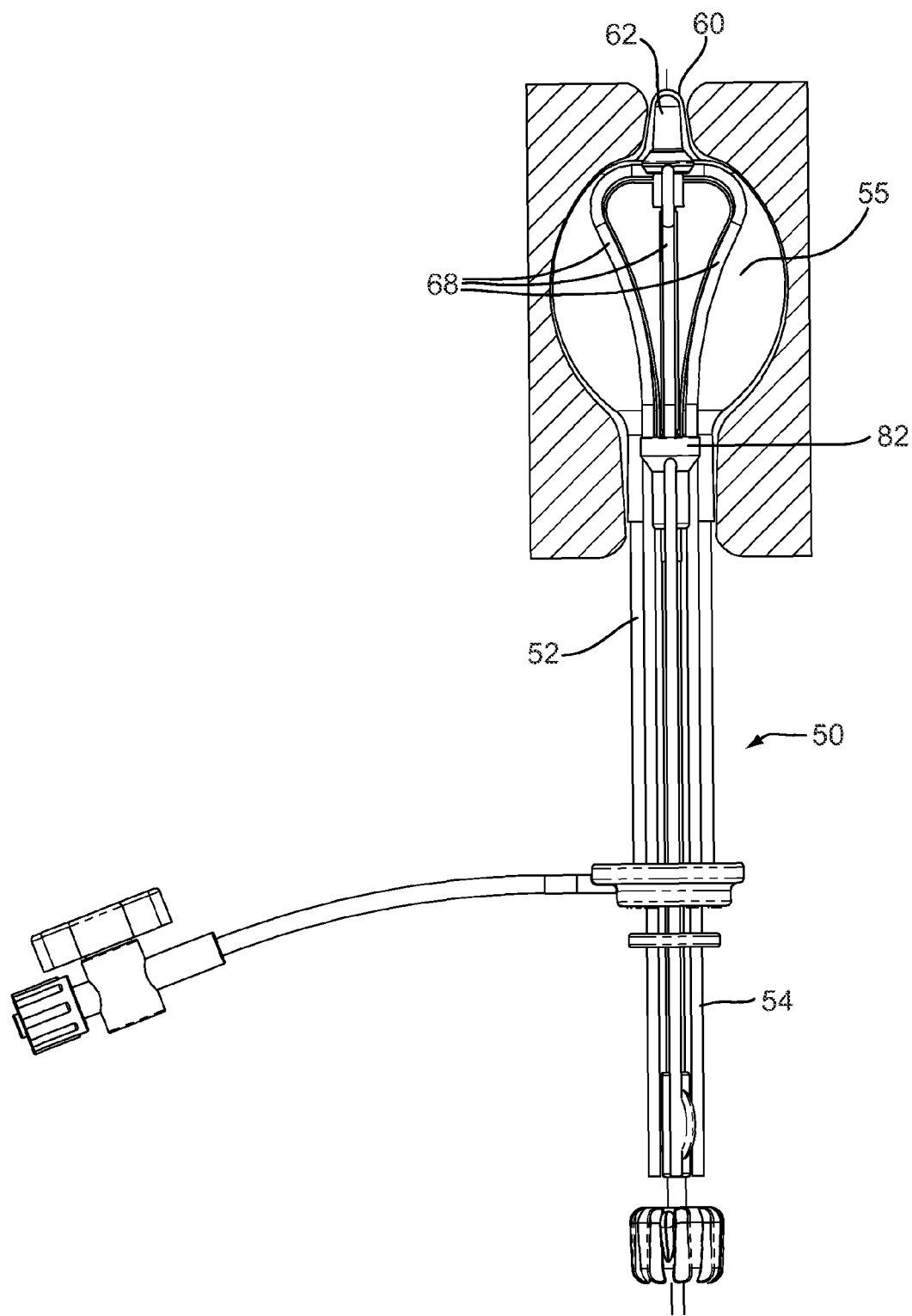
Figure 10:
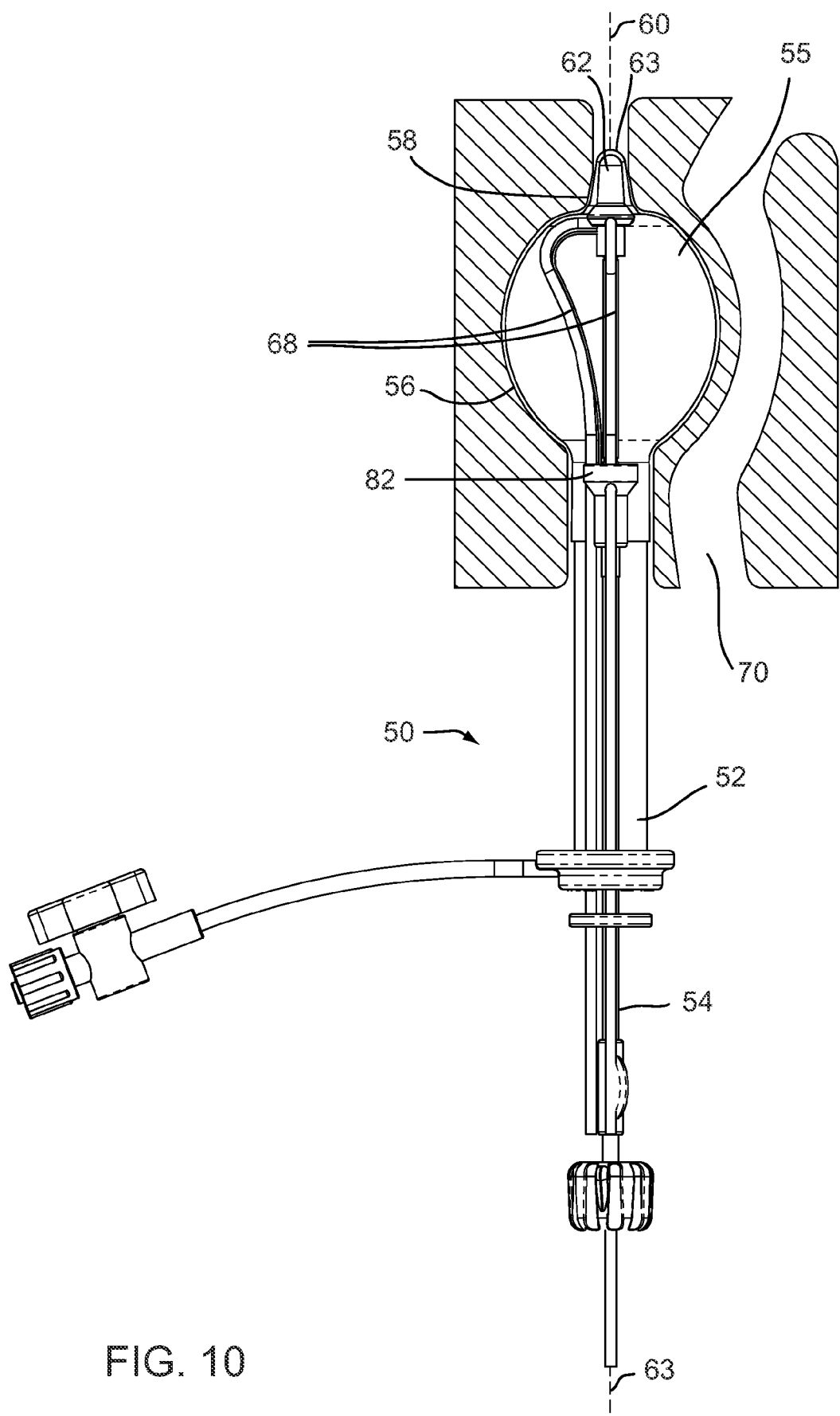
FIG. 10 is a partial cross-sectional side view of the patient's body and showing the access port device and applicator of FIGS. 9A and 9B.

Turning to FIGS. 9A, 9B, and 10, another embodiment of a system 50 is shown that may be used for treating cervical and/or uterine cancer. Generally, the system 50 includes a cavity access port device 52 and an applicator 54, which may be similar to the access port device 10 and applicator 16 described above. For example, the access port device 52 may include an expandable member 55, shown in FIG. 9A in a collapsed configuration and in FIGS. 9B and 10 in an expanded configuration. The access port device 52 may be configured for positioning within a vaginal cavity 56. Thus, the distal tip 60 of the access port device 52 may be sized for ease of placement within the external os 58 of the cervix, e.g., to substantially seal the cervix, thereby limiting fluid flow through the os 58 during treatment.

With additional reference to 11A-12D, the expandable brachytherapy applicator 54 may include a plurality of catheters or other elongate members 68 disposed around a center catheter 72, generally similar to the previous applicator 10. The applicator 54 may include a distal tip 62 sized for positioning within the distal tip 60 of the access port device 52, e.g., for ease of placement and localized delivery of radiation at the os and/or the cervix. Construction of the components of the applicator 54 may be generally similar to the applicators found in the applications incorporated by reference elsewhere herein.

The expandable portions of the catheters 68 may be coupled to an actuation hub 82 and a distal end of the center catheter 72. The actuation hub 82 and/or the distal tip 62 may be directed towards one another, thereby causing the catheters 68 to be subjected to an axially compressive force and to bow radially outwardly in a predetermined shape towards an expanded configuration. In an exemplary embodiment, the predetermined shape of the expanded configuration may conform to the tissue walls around the cervix in the vaginal cavity 56. The actuation hub 82 and/or the distal tip 62 may be directed apart from one another, thereby causing the catheters 68 to be pulled back radially inwardly towards a collapsed configuration. Further information regarding the mechanism and method for expanding and collapsing the catheters 68 may be found in the applications incorporated by reference elsewhere herein.

In the collapsed configuration, the catheters 68 may extend substantially parallel to the center catheter 72. However, the distal ends of the catheters 68 may have a slightly rounded shape where the distal tips of the catheters 68 curve slightly inward to attach to the center catheter 72, as shown in FIGS. 9A and 11A-11D.

In the expanded configuration, the expandable portions of the catheters 68 may be biased towards the cervix and/or uterus so that radiation applied through the catheters 68 may be preferentially directed distally towards the cervix and/or uterus, and away from surrounding, healthy tissue. In an exemplary embodiment, the expanded catheters 68 may form a pear shape that bulges near the distal tip 62 of the applicator 54 and tapers towards the actuation hub 82, as depicted in FIGS. 9B, 10, and 12A-12D.

The catheters 68 may expand radially outwardly into the pear shape, e.g., due to support members attached thereto and/or due to the configuration of the expandable catheters 68, as disclosed in the applications incorporated by reference herein. For example, as best seen in FIGS. 12A-12D, the catheters 68 may include one or more support members 66, e.g., extending at least partially along the expandable portions of the catheters 68. In an exemplary embodiment, the support members 66 may be elongate strips of material, e.g., metal, such as stainless steel or Nitinol, plastic, or composite material, that may be elastically deflected during use of the applicator 54, e.g., when the catheters 68 are directed between the collapsed and expanded configurations. In an alternative embodiment (not shown), the catheters 68 may have asymmetrical cross-sections providing a moment of inertia that biases the catheters 68 to expand radially outwardly in the predetermined manner, as disclosed in the applications incorporated by reference herein.

For further protection of healthy, non-target tissue, the catheters 68 may be arranged asymmetrically around the center catheter 72. In an exemplary embodiment, the applicator 54 may include three catheters 68 positioned substantially on one side of a plane extending parallel to a central longitudinal axis 63 defined by the center catheter 72. For example, as best seen in FIG. 10, the catheters 68 may lie within or above a plane extending along the longitudinal axis 63, thereby providing an asymmetrical arrangement. In combination with proper rotational orientation when inserted into the access port device 52, the catheters 68 may be oriented away from the rectum during use, e.g., to protect rectal tissue 70 from radiation exposure.

In a method for using the system 50, with the access port device 52 and the applicator 54 in their collapsed configurations, the access port device 52 and the applicator 54 may be introduced into the vaginal cavity 56 (successively or simultaneously, similar to the methods described above) until the distal tip 60 of the access port device 52 and the distal tip 62 of the applicator 54 are positioned within the external os 58 of the cervix, as shown in FIG. 9A. For example, similar to the methods described above, the access port device 52 may be inserted first with the expandable member 55 collapsed, and the applicator 54 may be inserted into the access portion device 52 with the expandable member 55 remaining collapsed. Alternatively, the applicator 54 may be inserted into the access portion device 52 outside the patient's body, and the access port device 52 and applicator 54 may be inserted at the same time.

The expandable member 55 of the access port device 52 may then be inflated. Alternatively, the access port device 52 may be inserted and the expandable member 55 inflated before inserting the applicator 54. When the expandable member 55 is inflated, the vaginal cavity 56 may be dilated, e.g., to push healthy, non-target tissue away from the applicator 54, which may protect the healthy non-target tissue from substantial radiation exposure during treatment. This may be particularly useful in cervical and/or uterine cancer treatment so that sensitive tissue, e.g., the vaginal walls and rectum, may be protected from substantial radiation exposure and damage.

After the expandable member 55 is inflated, the expandable catheters 68 of the applicator 54 may be directed to the expanded configuration, as shown in FIGS. 9B and 10, e.g., by directing the actuation hub 82 towards the distal tip 62. The method for expanding the catheters 68 may be substantially similar to the method for expanding the catheters 26 of the applicator 16 (e.g., as shown in FIGS. 5-7B), which method is discussed in greater detail in the applications incorporated by reference herein.

With the access port device 52 and the applicator 54 in their expanded configurations, radiation may be delivered to the target location adjacent to the body cavity. Specifically, in the exemplary embodiment, radiation may be delivered to tissue, e.g., to the cervix and/or the uterus (not shown), adjacent to the vaginal cavity 56. As described in the applications incorporated by reference herein, the lumens of the catheters 68 and 72 may define pathways for receiving radiation source(s). One or more radiation sources (not shown) may be directed into the lumens of the catheters 68 and 72 to deliver radiation to the tissue surrounding the cavity 56, which, due to the biased shape of the expanded applicator 54, is preferentially delivered to the cervix and/or the uterus.

Alternatively, one or more HDR sources may be delivered sequentially into the expandable catheters 68 and/or the center catheter 72, as described in the applications incorporated by reference herein. For example, an HDR source may be introduced into a first expandable catheter 68, advanced to a first position, and maintained at the first position for a predetermined time. The HDR source may then be advanced and/or retracted to a second position, and maintained there for a predetermined time, etc. The HDR source may then be removed from the first expandable catheter 68, and then introduced sequentially into each of the other expandable catheters 68 in a similar manner. In a further alternative, one or more radiation sources may be preloaded or secured within the expandable catheters 68 before introduction into the cavity 56. Additional information on use of the applicator 54 may be found in the applications incorporated by reference herein.

Turning to FIGS. 13A-14D, another exemplary embodiment of an expandable brachytherapy applicator 150 is shown, which includes a plurality of expandable catheters 168 disposed around a center catheter 172, which may be constructed similar to the applicators described above and disclosed in the applications incorporated by reference elsewhere herein. The applicator 150 may also include a center catheter handle 152 fixedly coupled to the center catheter 172, a catheter ring 154 for maintaining the positions of the expandable catheters 168 relative to one another and relative to the center catheter 172, an actuator 182, a catheter sleeve 184, and a distal tip 162. In FIGS. 13A-13D, the applicator 150 is shown in a collapsed configuration in which distal ends 170 of the catheters 168 are constrained within the catheter sleeve 184. In FIGS. 14A-14D, the applicator 150 is shown in an expanded configuration in which the distal ends 170 are exposed or otherwise deployed from the catheter sleeve 184 and expand transversely away from the center catheter 172.

The actuator 182 may be fixedly coupled to the expandable catheters 168 and slidably coupled to the center catheter 172. Thus, the center catheter 172 may slide axially relative to the actuator 182, e.g., through a central opening (not shown) in the actuator 182. The applicator 150 may further include an expansion tool (not shown) that may be selectively coupled to the actuator 182 from a proximal end of the applicator 150, e.g., for operating the actuator 182 to direct the distal ends 170 of the catheters 168 between the collapsed and expanded configurations. For example, the expansion tool may be removably coupled to the actuator 182 and/or the proximal end of the applicator 150, similar to expansion tools disclosed in the applications incorporated by reference elsewhere herein.

The catheter sleeve 184 and the distal tip 162 may be coupled or integrally formed together, e.g., with a tapered transition 164 therebetween. The tapered transition 164 may include one or more openings 186 therein, e.g., a plurality of openings 186 sized for receiving the distal ends 170 of respective catheters 168 therethrough. The proximal end of the catheter sleeve 184 may include an enlarged shoulder portion 188, which may be attached to or integrally formed with the catheter sleeve 184. For example, the distal tip 162, tapered transition 164, catheter sleeve 184, and shoulder 188 may be integrally molded as a single component, or may be formed from separate components that are attached together, e.g., using an interference fit, cooperating connectors, bonding using adhesive, sonic welding, and the like.

In the collapsed configuration, shown in FIGS. 13A-13D, the expandable catheters 168 may be substantially parallel to the center catheter 172 and may be positioned within the catheter sleeve 184 with the distal ends 170 of the catheters 168 adjacent to the openings 186 in the tapered transition 164 of the catheter sleeve 184. In the expanded configuration, shown in FIGS. 14A-14D, the center catheter 172 may be remain positioned within the sleeve 184 while the distal ends 170 of the catheters 168 may extend out of the openings 186 in the catheter sleeve 184.

In an exemplary embodiment, the distal ends 170 of the catheters 168 may be unattached and configured to expand transversely or radially outwardly away from the center catheter 172 in a predetermined manner upon being deployed from the catheter sleeve 184. For example, the distal ends 170 of the catheters 168 may be biased to curve radially outwardly into the expanded configuration, e.g., due to support members 166 attached thereto and/or due to the construction of the catheters 168 themselves, as described in the applications incorporated by reference elsewhere herein.

For example, as best seen in FIGS. 13B and 14B, the catheters 168 may include one or more support members 166, e.g., extending at least partially along the expandable distal ends 170 of the catheters 168. In an exemplary embodiment, the support members 166 may be elongate strips of material, e.g., metal, such as stainless steel or Nitinol, plastic, or composite material, that may be elastically deflected during use of the applicator 150, e.g., when the distal ends 170 are directed between the collapsed and expanded configurations. Alternatively, the catheters 168 may have asymmetrical cross-sections providing a moment of inertia that biases the catheters 168 to bend or curve radially outwardly in the predetermined manner, as disclosed in the applications incorporated by reference herein.

In a method for expanding the catheters 168, a user may grasp the center catheter handle 152 to maintain the position of the center catheter 172 while simultaneously directing the actuator 182 distally towards the catheter sleeve 184 until the actuator 182 contacts the enlarged shoulder portion 188 of the sleeve 184, as shown in FIGS. 14A-14D. Distal movement of the actuator 182 away from the handle 152 may cause distal movement of the expandable catheters 168 relative to the center catheter 172. When the expandable catheters 168 are directed distally, the unattached distal ends 170 of the catheters 168 may be deployed distally out of the openings 186 in the sleeve 184. As discussed above, the distal tips 170 of the catheters 168 may be biased towards an outwardly curved shape. Thus, as the distal ends 170 extend out of the openings 186 and escape the constraint of the catheter sleeve 184, the distal ends 170 may bend radially outwardly away from the center catheter 172.

To collapse the catheters 168, a user may grasp the handle 152 and retract the actuator 182 proximally towards the handle 152. Proximal movement of the actuator 182 may cause the catheters 168 to retract proximally back into the catheter sleeve 184. As the catheters 168 are retracted, the sleeve 184 may force the distal ends 170 back into the collapsed, substantially parallel configuration shown in FIGS. 13A-13D. Movement of the actuator 182 may be controlled by an expansion tool removably coupled to the proximal end of the applicator 150, as discussed above.

The applicator 150 may be part of a system, e.g., including a tubular delivery device, such as a catheter, cannula, trocar, obturator, and/or needle (not shown), for introducing the applicator 150 into a target location, e.g., as described in the applications incorporated by reference elsewhere herein. For example, for treating cervical and/or uterine cancer, the applicator 150 may be part of a system that may include an access port device, e.g., similar to the access port device 10 in FIGS. 1 and 2 and/or to the access port device 52 in FIGS. 9A, 9B and 10.

A method for using such a system may be substantially similar to the method for using the system 50 depicted in FIGS. 9A, 9B and 10. For example, an access port device (not shown) may be introduced into a vaginal cavity with an expandable member on a distal end thereof in a collapsed configuration. The applicator 150 may be positioned within the access port device before or after introducing the access port device into the vaginal cavity, e.g., for simultaneous or successive introduction of the access port device and the applicator 150. Optionally, the applicator 150 may be introduced into the vaginal cavity after the access port device has been fully inserted, and before or after the expandable member has been inflated, as described above.

After the applicator 150 is introduced and the expandable member of the access port device is inflated, the actuator 182 may be directed distally towards the catheter sleeve 184, thereby pushing the catheters 168 out of the catheter sleeve 184 and causing the distal ends 170 to expand transversely away from the center catheter 172. For example, the distal ends 170 may curve outwardly such that the ends abut (through the access port device) the cervix of the patient being treated without substantial contact with the vaginal walls. After expanding the distal ends 170 of the catheters 168, radiation may be applied through the catheters 168 and 172 similar to the previous embodiments. Due to the outwardly curved shape of the expanded distal ends 170 of the catheters 168, radiation may be directed towards the target tissue and away from healthy tissue. In this embodiment, the target tissue may be cervical tissue and/or uterine tissue.

After the radiation treatment is applied, the distal ends 170 of the catheters 168 may be retracted proximally into the catheter sleeve 184 by pulling the actuator 182 proximally away from the sleeve 184. The collapsed applicator 150 may then be withdrawn from the access port device. The access port device may subsequently be deflated and withdrawn from the vaginal cavity immediately or after multiple treatments with the same or different applicator, similar to the previous embodiments.

Turning to FIGS. 19A-20B, another exemplary embodiment of an expandable brachytherapy applicator 250 is shown that includes a plurality of expandable catheters 268, e.g., two catheters 268, disposed adjacent a center catheter 272. The applicator 250 may be constructed generally similar to the other embodiments described herein and in the applications incorporated by reference above, e.g., using similar materials and methods. Generally, the applicator 250 includes an expandable distal portion 254, which may be introduced into a body cavity or other target tissue region, and a proximal portion 252, which may extend from the target tissue region out of a patient's body during use, e.g., to allow one or more sources of radiation (not shown) to be introduced into the catheters 268, 272, similar to the previous embodiments.

As shown in FIGS. 20A and 20B, the applicator 250 includes a distal tip 262 sized for positioning within an os 58 of a cervix and/or within a tip of an access device (not shown), e.g., similar to the previous embodiments. As best seen in FIGS. 19B and 19D, distal ends of the catheters 268, 272 may be coupled to the distal tip 262 and/or to each other, e.g., by interference fit and/or connectors (not shown) within the distal tip 262, by bonding with adhesives, sonic welding, fusing, and the like. The expandable catheters 268 may be coupled to a hub 282, while the center catheter 272 may be slidable through or otherwise movable relative to the hub 282. Thus, the hub 282 and/or the distal tip 262 may be directed towards one another, thereby causing expandable portions 268a of the expandable catheters 268 (i.e., between the hub 282 and distal tip 262) to be subjected to an axially compressive stress. This stress causes the expandable portions 268a to bow radially outwardly from a collapsed, e.g., axial, configuration (shown in FIGS. 19A and 19B) to an expanded configuration (shown in FIGS. 19C and 19D). Conversely, the hub 282 and the distal tip 262 may be directed apart from one another, thereby causing the expandable portions 268 of the catheters 268 to be pulled back radially inwardly towards the collapsed configuration.

As shown in FIGS. 19A and 19B, in the collapsed configuration, the expandable portions 268a of the catheters 268 may extend substantially parallel to the center catheter 272. As shown in FIGS. 19C and 19D, the expandable portions 268a of the catheters 268 may expand away from one another substantially within a plane, i.e. to define a substantially planar shape in the expanded configuration. The central catheter 272 may be offset below the plane defined by the catheters 268, e.g., such that the catheters 268 are offset asymmetrically from a central axis of the central catheter 272, similar to the previous embodiments.

Optionally, as best seen in FIGS. 19B and 19D, at least the expandable portions 268a of the catheters 268 may include one or more support members 266, e.g., attached to or otherwise extending at least partially along the expandable portions 268a. The support members 266 may bias the expandable portions 268a of the catheters 268 to remain substantially within the desired plane during expansion and contraction with minimal lateral movement out of the plane. In an exemplary embodiment, the support members 266 may be elongate strips of material, e.g., metal, such as stainless steel or Nitinol, plastic, or composite material, that may be elastically deflected during use of the applicator 250, e.g., when the catheters 268 are directed between the collapsed and expanded configurations.

The applicator 250 includes an actuator 280, e.g., on the proximal portion 252 of the applicator 250, for directing the expandable portions 268a of the catheters 268 between the collapsed and expanded configurations. For example, as shown in FIGS. 19A and 19C, the actuator 280 may include a handle 284 coupled to the hub 282, e.g., by shaft 273, and a plunger 286 coupled to the center catheter 272. The shaft 273 may be substantially rigid and/or axially incompressible (e.g., but bendable) such that the distance between the hub 282 and the handle 284 remains substantially fixed. The shaft 273 may be a tubular body, e.g., including a lumen for slidably receiving the central catheter 272 therethrough (not shown). Alternatively, the central catheter 272 may slide or otherwise move adjacent to the shaft 273 rather than through the shaft 273.

The plunger 286 may be movable relative to the handle 284, e.g., slidable axially between a first or distal position (shown in FIG. 19A) and a second or proximal position (shown in FIG. 19C), to move the center catheter 272 relative to the shaft 273 and consequently relative to the expandable catheters 268. For example, as shown, the plunger 286 may include a piston or other elongate member 287 that is slidable a predetermined distance into and out of the handle 284, thereby limiting motion of the plunger 286 between the first and second positions.

Optionally, the plunger 286 may be biased to one of the first and second positions, e.g., by a spring 288 between the plunger 286 and handle 284. As shown, the spring 288 may be a compression spring located between the handle 284 and plunger 286 (e.g., on a shaft, not shown), although alternatively, the spring may be located inside the handle 284 (not shown), e.g., coupled to the piston 287. In addition or alternatively, the handle 284 may include a locking pin 285, which may be selectively engaged with the plunger 286 to selectively lock the plunger 286 in a desired position. For example, the locking pin 285 may create an interference fit with the piston 287 when engaged, or the locking pin 285 may be received in one or more apertures (not shown) in the piston 287 to lock the plunger 286. It will be appreciated that other locking mechanisms may be provided between the handle 284 and plunger 286, as desired.

As shown in FIG. 19C, the spring 288 may bias the plunger 286 to the second position, where the expandable catheters 268 are in the expanded configuration. The bias of the spring 288 may be overcome by directing the plunger 286 to the first position and then engaging the locking pin 285 to lock the plunger 286 in the first position, as shown in FIG. 19A. Optionally, the locking pin 285 may be engaged in the second position (or any other intermediate position, if desired), e.g., to prevent inadvertent collapse of the expandable catheters 268 during use.

Turning to FIGS. 20A and 20B, during use, the applicator 250 may be introduced into a vaginal cavity 56 (or a lumpectomy cavity or other target tissue region) with the catheters 268 in the collapsed condition, similar to the other embodiments herein. Optionally, the applicator 250 may be introduced with or through an access device (successively or simultaneously), similar to the other embodiments herein. As shown, the applicator 250 may be introduced until the distal tip 262 is positioned within the external os 58.

In addition, the applicator 250 may be manipulated to orient the expandable portions 268a of the catheters 268 in a desired orientation. For example, similar to the previous embodiments, it may desirable to orient the expandable portions 268a towards the cervix and/or vaginal wall and/or away from the rectum 70 or other regions of the target tissue region. As best seen in FIG. 20B, for example, the applicator 250 may be rotated to orient the expandable catheters 268 away from the rectum 70, i.e., with the center catheter 272 disposed between the expandable catheters 268 and the rectum 70. Thus, the plane of expansion of the expandable portions 268a of the catheters 268 may be oriented laterally relative to the patient's body and not anteriorly or posteriorly.

With the applicator 250 oriented in a desired manner, the expandable portions 268a of the catheters 268 may be directed to the expanded configuration, as shown in FIGS. 20A and 20B. As explained above, if the locking pin 285 of the actuator 280 is locking the plunger 286 in the first position (with the expandable portions 268a in the collapsed configuration), the applicator 250 may be actuated simply by releasing the locking pin 285. Once released, the spring 288 may then bias the plunger 286 and consequently the center catheter 272 to move proximally relative to the expandable catheters 268 to axially compress and expand the expandable portions 268a. Thus, the distal tip 262 of the applicator 250 may remain substantially stationary, e.g., within the os 58 of the cervix, which may facilitate stabilization of the applicator 250 during use.

With the applicator 250 in the expanded configurations, radiation may be delivered to the tissue adjacent the applicator 250, e.g., to the cervix and/or the uterus adjacent to the vaginal cavity 56. As described elsewhere herein and in the applications incorporated by reference herein, the lumens of the catheters 268 and 272 may define pathways for receiving radiation source(s). One or more radiation sources (not shown) may be directed into the lumens of the catheters 268 and 272 to deliver radiation to the tissue surrounding the cavity 56 in accordance with a desired dose plan.

Once sufficient treatment is performed, the applicator 250 may be returned to the collapsed configuration, e.g., by advancing the plunger 286 and then engaging the locking pin 285. The collapsed applicator 250 may then be removed from the vaginal cavity 56 and patient's body. If an access device remains within the vaginal cavity 56, another applicator (or the same applicator) may be introduced using the access device for one or more subsequent treatments.

In other exemplary embodiments, in any of the treatment systems described herein, other access devices may be provided, e.g., for expanding, dilating, creating, and/or otherwise lining a tissue tract or other passage through tissue, e.g., that leads to a body cavity or other target treatment location, to facilitate introduction of one or more instruments.

Turning to FIGS. 15A-15E, an exemplary embodiment of such an access sheath 200 is shown that generally includes a distal portion 202 sized for introduction into a passage through tissue, a bendable intermediate section 204, and a proximal portion 206. The access sheath 200 may include a wall that at least partially defines a lumen 212 that extends between the proximal and distal portions 206, 202 of the access sheath 200. Optionally, the proximal portion 206 of the access sheath 200 may include a pull tab, handle, or other feature, which may facilitate manipulation, e.g., advancing, retracting, and/or bending, the access sheath 200 during use.

As shown, the passage 212 of the access sheath 200 is defined by a generally "C" shaped wall that includes longitudinal edges 211 that define a gap 208. The wall may be biased to the "C" shape, yet resiliently deflectable to allow the longitudinal edges 211 to separate or otherwise move, e.g., to increase a diameter of the passage 212, a width of the gap 208, and/or otherwise adjust a shape of the access sheath 200.

Thus, the access sheath 200 may accommodate receiving one or more instruments (not shown) through the gap 208 and/or the access sheath 200 may be easily removable from around an instrument received within the passage 212.

Figure 15A:
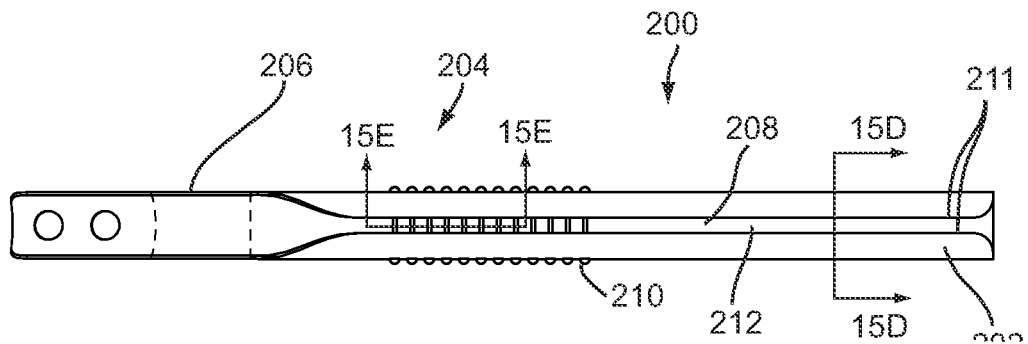
FIGS. 15A and 15B are top and side views, respectively, of an exemplary embodiment of an access sheath for use in a brachytherapy system.
Figure 15B:
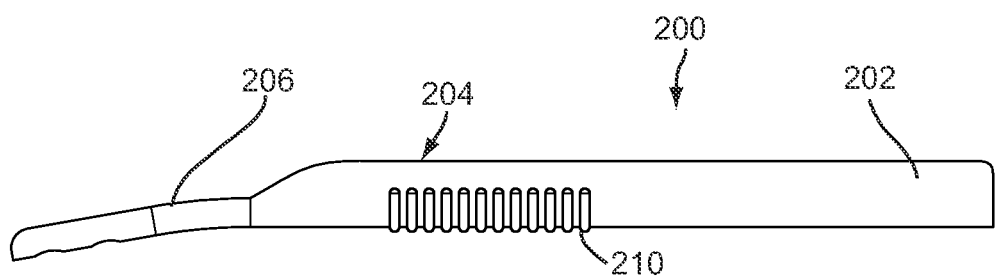
Figure 15C:
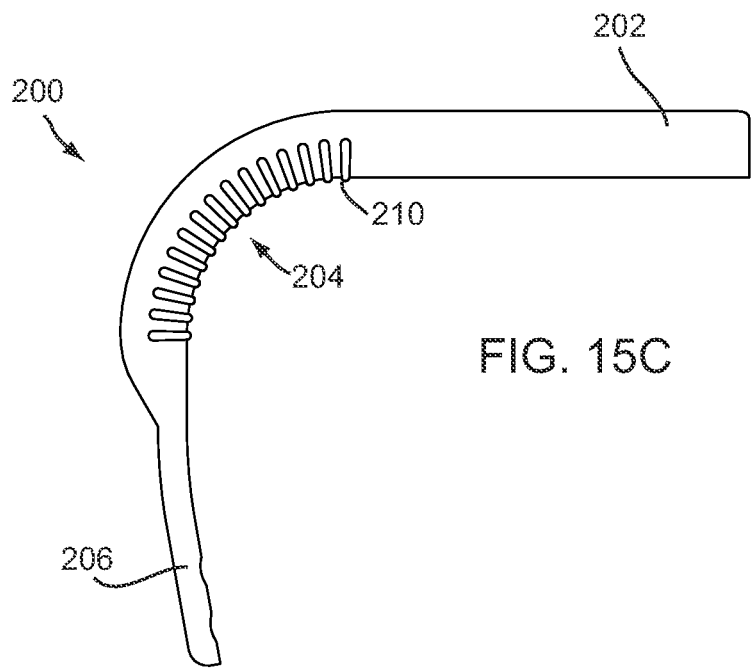
FIG. 15C is a side view of the access sheath of FIGS. 15A and 15B with a bendable section of the access sheath directed to a bent configuration.
Figure 15D:
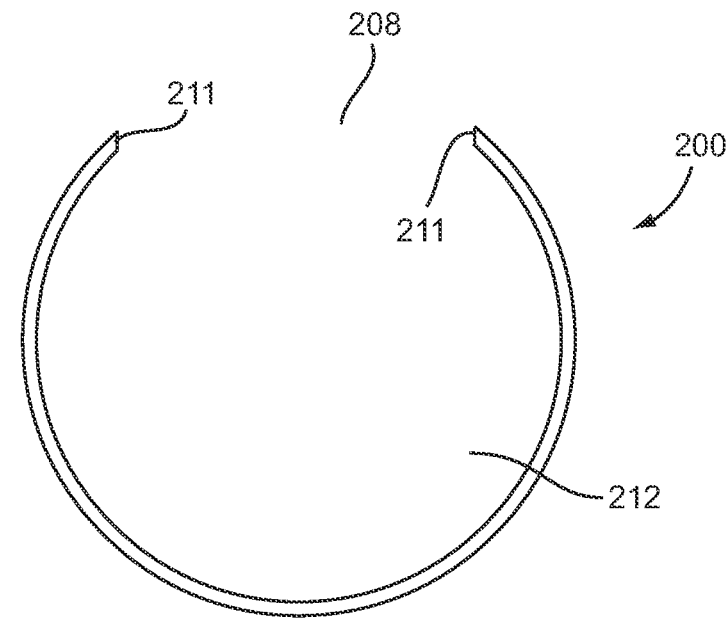
FIGS. 15D and 15E are cross-sectional views of the access sheath taken along lines 15D-15D and 15E-15E, respectively, in FIG. 15A.
Figure 15E:
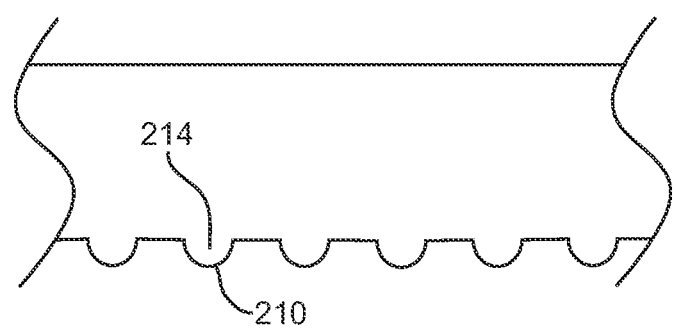
Figure 16A:
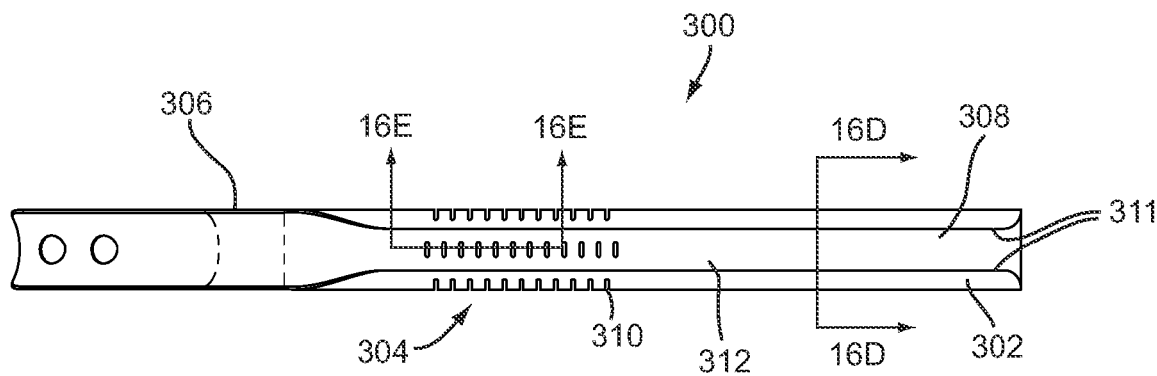
FIGS. 16A and 16B are top and side views, respectively, of another exemplary embodiment of an access sheath for use in a brachytherapy system.
Figure 16B:
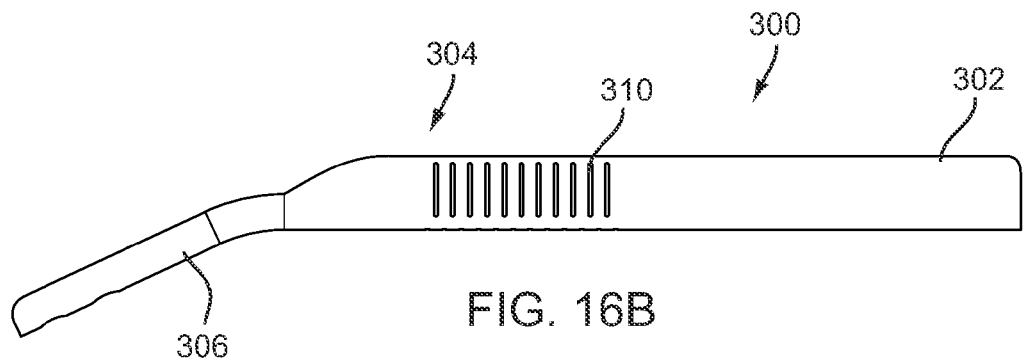
Figure 16C:
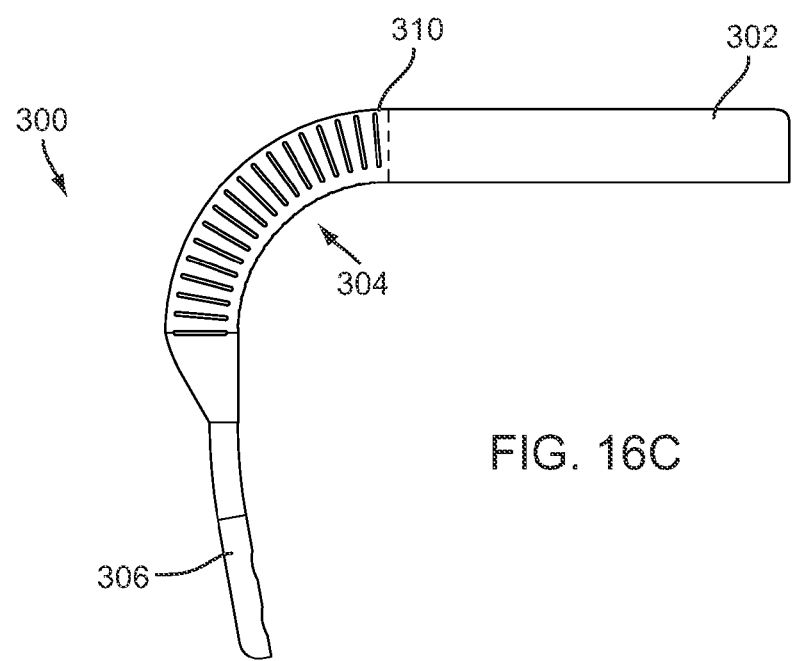
FIG. 16C is a side view of the access sheath of FIGS. 16A and 16B with a bendable section directed to a bent configuration.
Figure 16D:
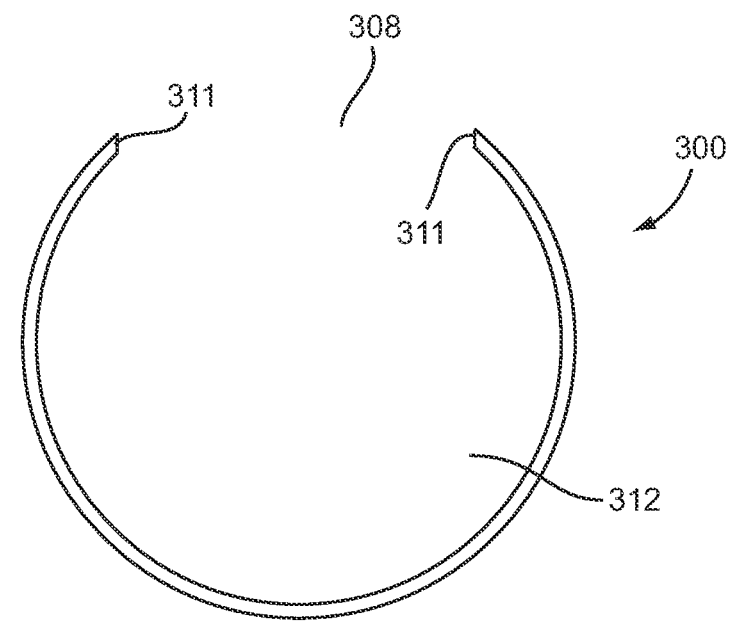
FIGS. 16D and 16E are cross-sectional views of the sheath taken along lines 16D-16D and 16E-16E, respectively, in FIG. 16A.
Figure 16E:
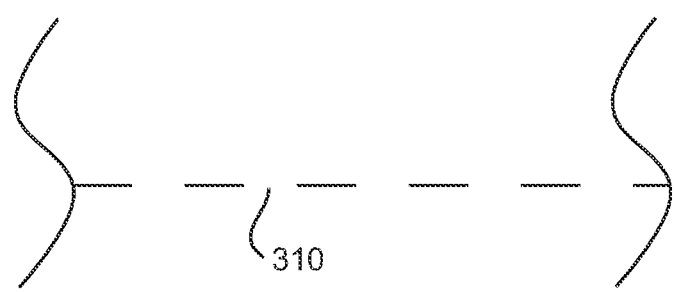

In the embodiment shown in FIGS. 15A-15E, the bendable section 204 may include a plurality of ridges or corrugations 210 that extend partially around the circumference of the access sheath 200. The ridges 210 may impart increased flexibility to the bendable section 204 relative to the distal and proximal portions 202, 206 of the access sheath 200, e.g., to allow the bendable section 204 to curve or otherwise bend in a desired manner. For example, as shown in FIG. 15E, the ridges 210 may protrude outwardly from an outer surface of the access sheath 200 and/or may be hollow so as to form troughs 214 on an inner surface of the sheath 200. The number, size, and/or spacing of the ridges 210 may be selected to make the bendable section 204 flexible enough to bend to a desired degree, e.g., to at least approximately a ninety degree (90°) angle between the proximal and distal portions 206, 202 of the access sheath 200, as illustrated in FIG. 15C. Other angles greater or less than ninety degrees (90°) may also be possible, if desired, depending upon the material and construction of the ridges 210 or other features of the bendable section 204.

In alternate embodiments, the access sheath 200 may include other features that impart increased flexibility to the bendable section 204. For example, as shown in FIGS. 16A-16E, another exemplary embodiment of an access sheath 300 is shown that includes a bendable section 304 including a plurality of slots 310 cut or otherwise formed through the wall of the access sheath 300 for increasing the flexibility of the bendable section 304 relative to the proximal and distal sections of the sheath 300. Similar to the access sheath 200 in FIGS. 15A-15E, the access sheath 300 generally includes a semi-rigid distal portion 302, a proximal portion 306 including a pull tab, a lumen 312 extending therebetween, and longitudinal edges 311 defining a continuous gap 308 that extends between the proximal and distal portions 306, 302.

Optionally, the access sheath 300 (or the access sheath 200) may include a lubricious coating and/or other material, e.g., on an inner surface thereof to facilitate introduction of one or more instruments through the lumen 312 and/or on an outer surface thereof to facilitate advancement through tissue with minimal resistance. In addition, the lumen 312 of the sheath 300 may be sized for slidably receiving one or more instruments therethrough, e.g., an expandable dilation device 410, such as that shown in FIGS. 17A-17C, an access port device (not shown), such as that shown in FIGS. 1-2, and/or an applicator (also not shown), such as any of those described herein or in the references incorporated by reference herein.

Alternatively, if the diameter or other cross-section of the lumen 312 of the sheath 300 is smaller than the outer diameter of the instrument being introduced into the lumen 312, the gap 308 in the sheath 300 may widen, thereby expanding the diameter of the sheath 300 to accommodate the instrument.

Figure 17A:
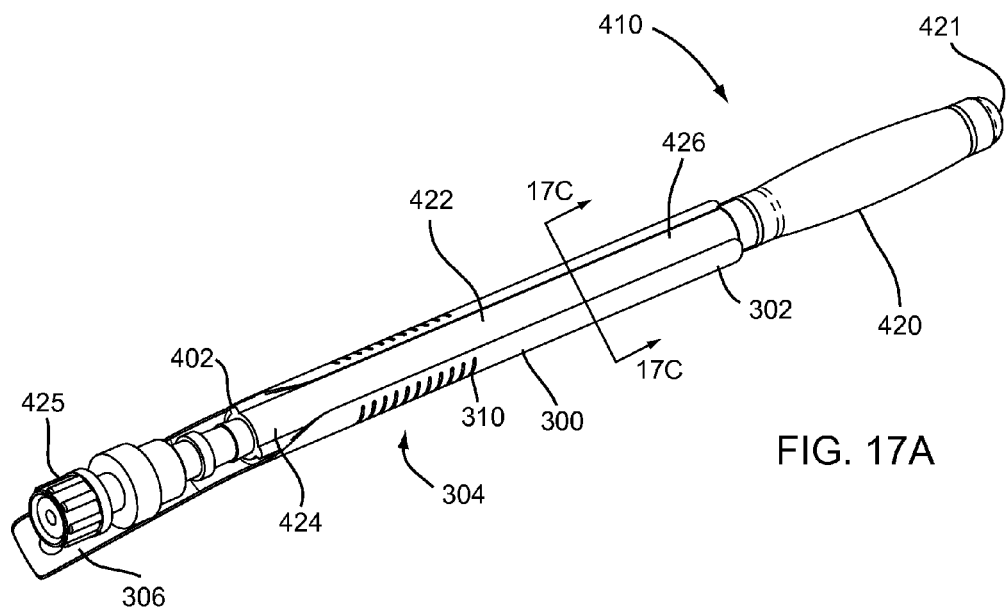
FIG. 17A is a perspective view of a brachytherapy system that includes an access sheath, such that shown in FIGS. 16A-16E, and an expandable device including a shaft received in a lumen of the access sheath.
Figure 17B:
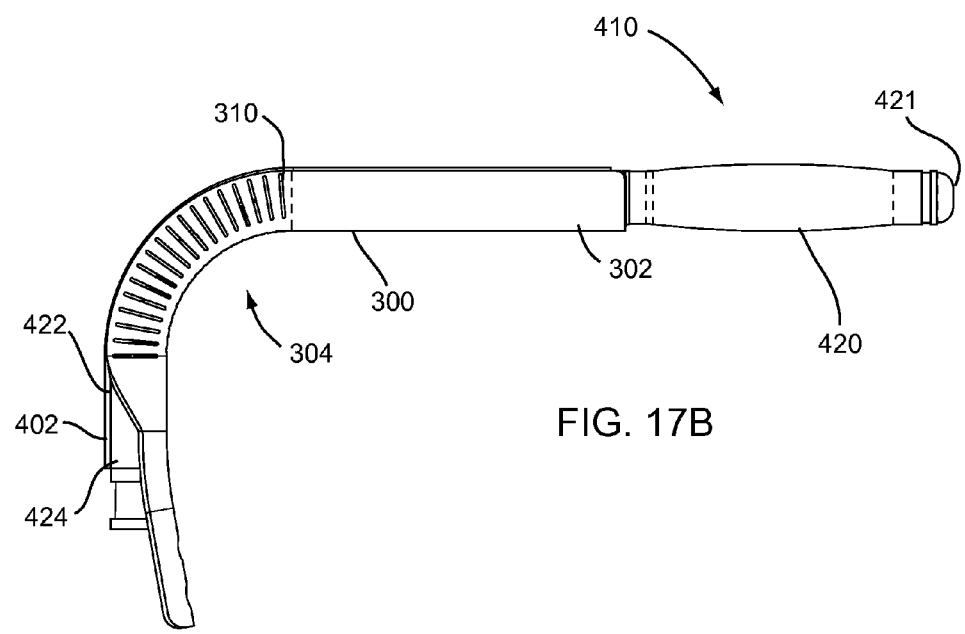
FIG. 17B is a side view of the brachytherapy system of FIG. 17A with the sheath and consequently the shaft of the expandable device directed to a bent configuration.

Turning to FIGS. 17A and 17B, an expandable dilation device 410 is shown that may be carried by or otherwise used in conjunction with the access sheath 300. Generally, the expandable device 410 includes an elongated shaft 422 including a proximal end 424, a distal end 426, and a balloon or other expandable member 420 on the distal end 426. The expandable member 420 may be constructed similar to the expandable member 5 on the access port device 10 shown in FIGS. 1-2 and described further elsewhere herein, e.g., formed from compliant or semi-compliant material expandable between collapsed and expanded conditions and terminating in a distal tip 421. The shaft 422 may also be constructed similar to the shaft 4 of the access port device 10, except that the shaft 422 may not include the ring 3 and working channel 8. Instead, the shaft 422 may include a single lumen (not shown) extending from a connector 425 on the proximal end 424, e.g., a Luer lock connector, to an interior of the expandable member 420.

In addition, as best seen in FIG. 17C, the shaft 422 includes one or more guide elements 402 (two shown) for cooperating with the longitudinal edges 311 of the access sheath 300, e.g., to maintain the expandable device 410 in a desired orientation relative to the access sheath 300. For example, the guide element(s) 402 may allow the shaft 422 of the expandable device 410 to be received within the lumen 312 of the access sheath 300 in a predetermined angular orientation, yet allow axial movement of the shaft 422 relative to the access sheath 300. As shown in FIG. 17B, the entire assembly, including the expandable device 410 and the access sheath 300, may be sufficiently flexible to bend, if desired, e.g., up to a ninety degree (90°) angle.

Figure 18B:
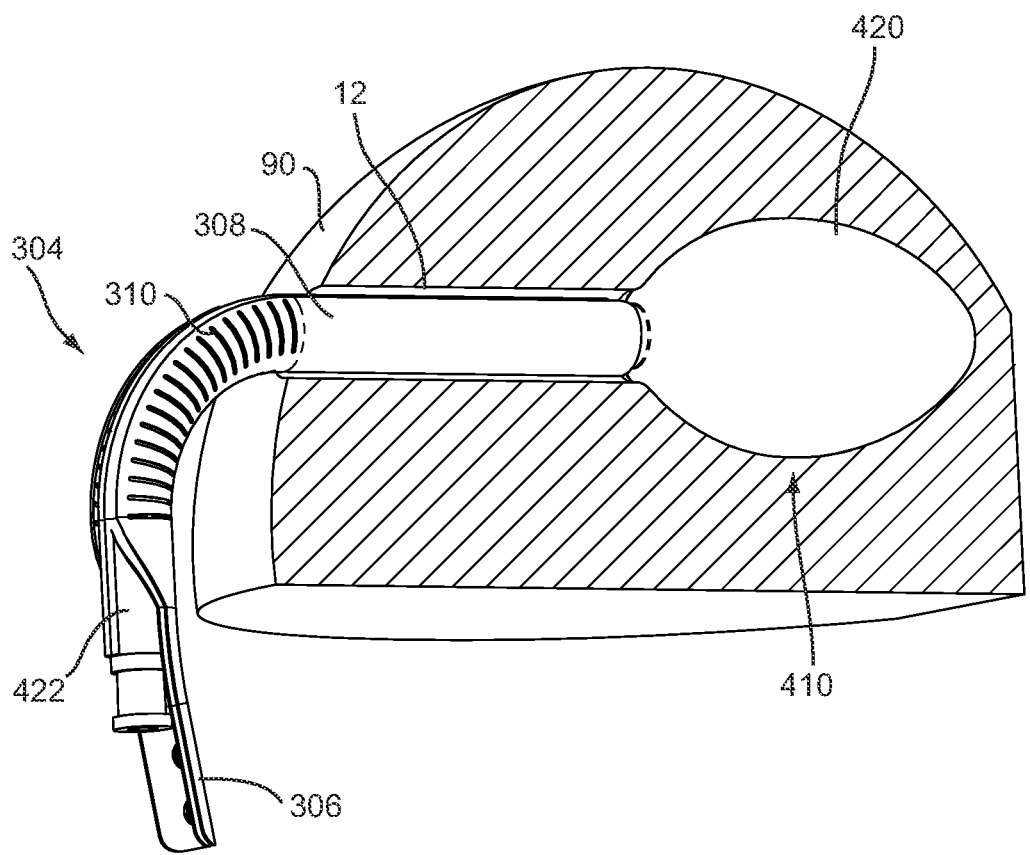
FIG. 18B shows an expandable member of the expandable device expanded to dilate tissue within the target tissue region and a bendable section of the access sheath directed to the bent configuration.
Figure 18C:
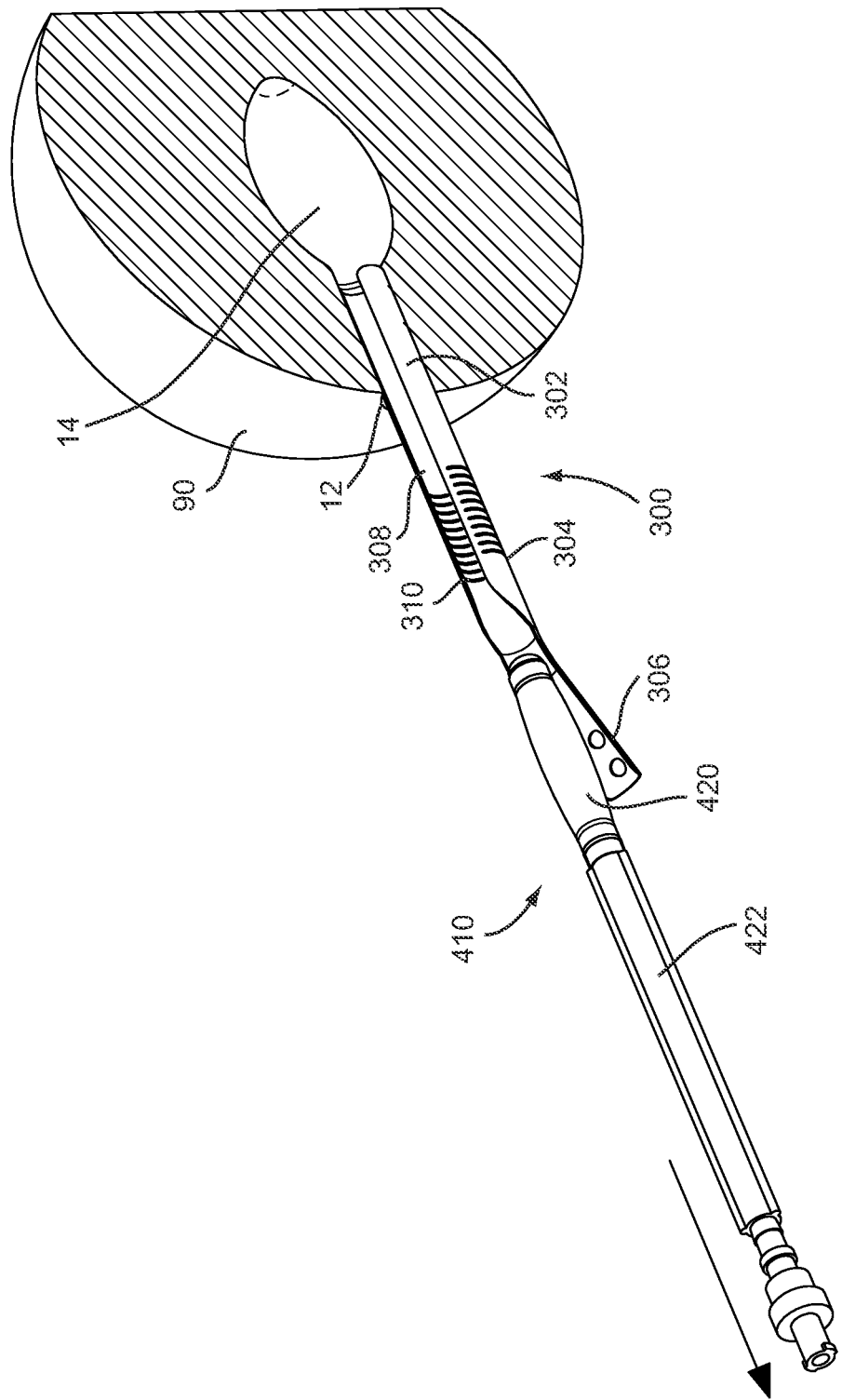
FIG. 18C shows the expandable device being removed from the access sheath after collapsing the expandable member.
Figure 18D:
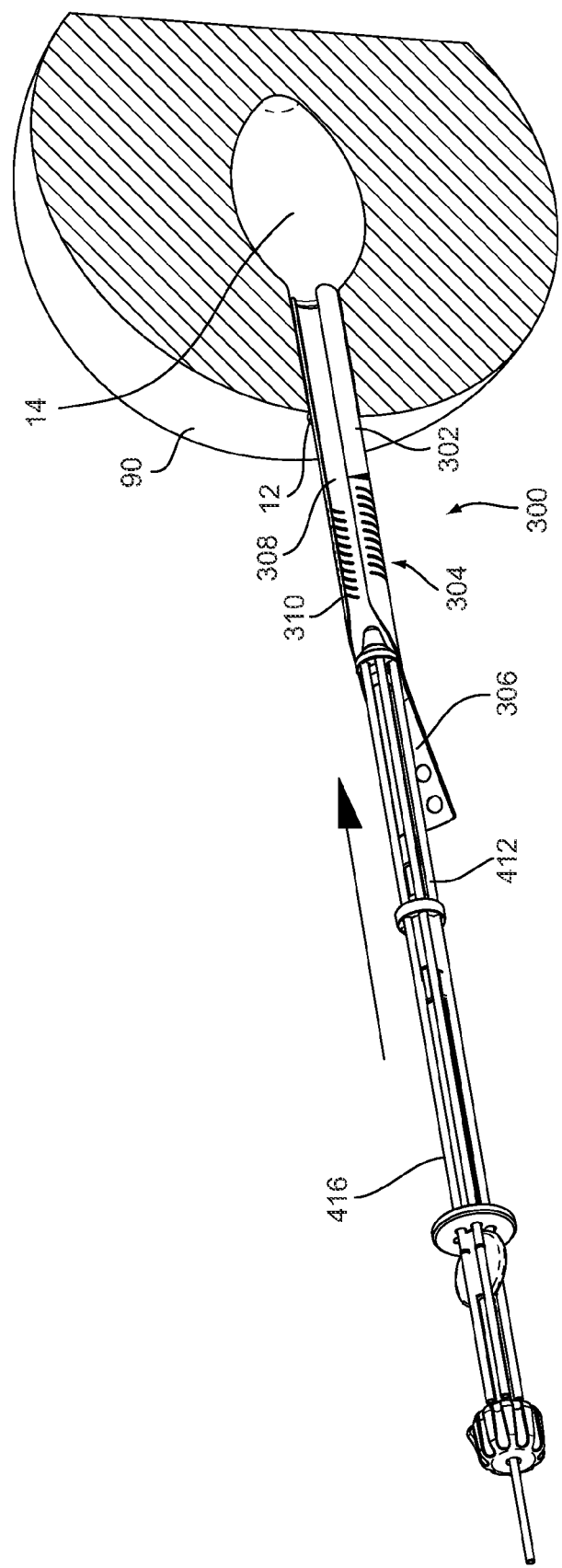
Figure 18F:
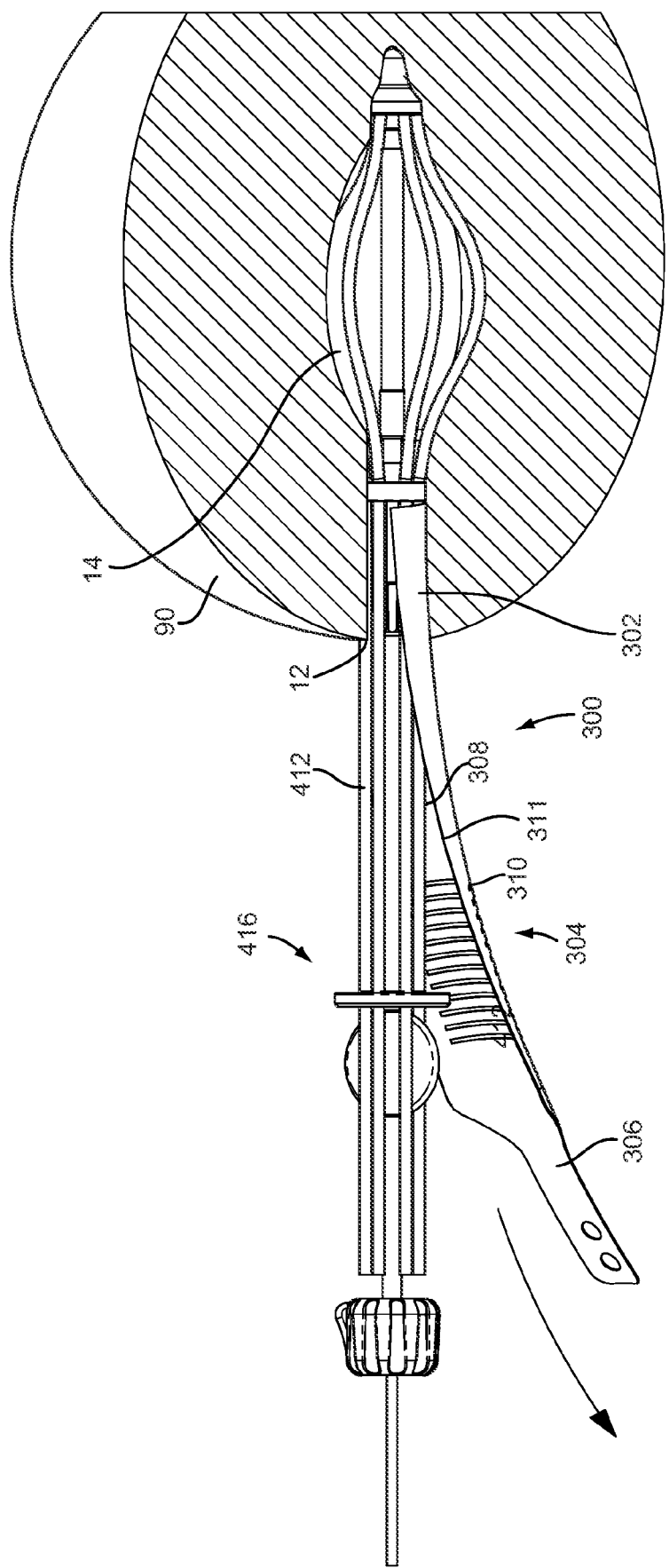
FIG. 18F shows the distal portion of the applicator being expanded within the target tissue region.

Turning to FIGS. 18A-18F, the access sheath 300 and expandable device 410 may be used during brachytherapy treatment of tissue within a target tissue region, e.g., also involving a brachytherapy treatment device, such as applicator 416 shown in FIGS. 18E and 18F. It will be appreciated, however, that the methods described herein may apply to using any of the brachytherapy treatment devices described elsewhere herein and in the references incorporated by reference herein, and should not be limited to the particular applicator 416 shown.

Initially, as shown in FIG. 18A, the expandable device 410 and access sheath 300 may be placed through a passage through tissue 12 into a body cavity or other target tissue region 14, e.g., a lumpectomy cavity within a breast 90, a vaginal cavity (not shown), and the like. In one embodiment, the sheath 300 may be introduced through the passage 12 until the distal portion 302 communicates with the body cavity 14. For example, using a needle, dilator and/or other device, the passage 12 may be created, although alternatively, the passage 12 may already exist, e.g., from a lumpectomy or other procedure. The access sheath 300 may be introduced into the passage 12, e.g., over a needle, dilator, and/or other device. Optionally, the access sheath 300 may be compressed to a smaller diameter, e.g., by at least partially overlapping the longitudinal edges 311, to facilitate introduction into the passage 12.

Once the access sheath 300 is positioned within the passage 12, the expandable device 410, with the expandable member 420 in the collapsed condition, may be introduced into the lumen 312 of the access sheath 300 and advanced until the expandable member 420 is disposed within the body cavity 14. For example, the guide element(s) 402 may be aligned with the longitudinal edges 311 of the access sheath 300 and the expandable device 410 may be advanced through the lumen 312 of the access sheath 300 until the expandable member 420 is positioned within the body cavity 14. The expandable device 410 may be advanced until the distal tip 421 of the expandable member 420 abuts a distal end of the body cavity 14 and/or until the entire expandable member 420 is positioned within the body cavity 14, as shown in FIG. 18A. If desired, the position of the expandable member 420 may be confirmed, e.g., using fluoroscopy, ultrasound, or other imaging, e.g., by providing markers (not shown) on the distal tip 421 and/or elsewhere on the expandable member 420 or expandable device 410.

Alternatively, the expandable device 410 may be received within the access sheath 300 before being introduced into the passage 12 and/or body cavity 14. For example, during manufacturing or immediately before a procedure, the expandable device 410 may be inserted into the lumen 312 of the access sheath 300, e.g., until the expandable member 420 is disposed beyond the distal portion 302 of the access sheath 300. In this alternative, the resulting assembly including the sheath 300 and the expandable device 410 (shown in FIGS. 17A-17C) may be advanced into the passage 12 together until the distal portion 302 of the sheath 300 is disposed adjacent the body cavity 14 and/or the expandable member 420 is disposed within the body cavity 14. In this alternative, the access sheath 300 and expandable device 410 may be advanced until the distal tip 421 of the expandable member 420 abuts a distal end of the body cavity 14 and/or until the entire expandable member 420 is positioned within the body cavity 14, also as shown in FIG. 18A, and optionally using external imaging.

The length of the access sheath 300 is such that the bendable section 304 of the access sheath 300 remains outside of the patient's body when the distal portion 302 of the access sheath 300 is advanced sufficiently to provide access to the body lumen 14. The access sheath 300 may remain in place for an indefinite period of time, e.g., after removing the expandable device 410 and/or the applicator 416 or leaving the expandable device 410 and/or applicator 416 within the body cavity 14. In these situations, the bendable section 304 of the access sheath 300 may be bent to place the external components against or immediate adjacent the breast 90 or the patient's skin if used at other locations.

When leaving the access sheath 300 in place during a procedure or for an extended period of time, e.g., with the expandable device 410 in place, as shown in FIG. 18B, the bendable section 304 of the sheath 300 may be bent or folded against the outside of the breast 90 to minimize contact with the external components, interference of the external components to other activities, and/or discomfort by the patient.

As shown in FIG. 18B, the expandable member 420 may be expanded within the body cavity 14, e.g., to engage and/or dilate surrounding tissue, similar to the access port device described above. The expandable member 420 may also be introduced into the access sheath 300 and body cavity after treatment, e.g., after removing the applicator 416, as described further below, to substantially seal the passage 12 between treatments.

Turning to FIG. 18C, after dilation of the tissue surrounding the body cavity 14, the expandable member 420 may be collapsed, and the expandable device 410 may be withdrawn from the body cavity 14 and access sheath 300. As shown, if the access sheath 300 is bent, the access sheath 300 may be returned to a straightened configuration, e.g., to facilitate removal of the expandable device 410. Alternatively, the access sheath 300 may remain in the bent configuration and the expandable device 410 may be removed by separating the longitudinal edges 311 of the access sheath 300, i.e., to widen the gap 308 sufficiently to accommodate removal of the expandable device 410.

Turning to FIGS. 18D and 18E, an applicator 416 may be inserted through the access sheath 300 and into the body cavity 14. As shown in FIG. 18D, the access sheath 300 may be in the straightened configuration to facilitate introducing the applicator 416 through the lumen 312 of the access sheath 300. The applicator 416 may be advanced through the access sheath 300 such that the longitudinal edges 311 of the access sheath 300 slidably engage catheters 412 of the applicator 416, as shown in FIG. 18G. In this manner, the access sheath 300 may function to hold the catheters 412 of the applicator 416 together during introduction of the applicator 416 and/or maintain the applicator 416 in a desired angular orientation during introduction through the access sheath 300.

When an expandable distal portion of the applicator 416 is positioned within the body cavity 14, the applicator 416 may be expanded, as shown in FIG. 18F. The catheters 412 of the applicator 416 may remain engaged with the longitudinal edges 311 of the access sheath 300, thereby minimizing movement of the catheters 412 during treatment.

Alternatively, as shown in FIG. 18F, once the applicator 416 is positioned in a desired location within the body cavity 14, the access sheath 300 may be removed from around the applicator 416. For example, a pull tab on the proximal end 306 of the access sheath 300 may be pulled, thereby separating the longitudinal edges and opening the gap 308 in access sheath 300 sufficiently to remove the access sheath 300 without substantially disturbing the applicator 416.

With the applicator 416 in the expanded configuration (either with the access sheath 300 removed or remaining), radiation may be delivered to tissue adjacent the body cavity 14, e.g., similar to embodiments and methods described elsewhere herein and in the references incorporated by reference.

If the applicator 416 is to remain in place between fractions of treatment, the applicator 416 may be bent in conjunction with the access sheath 300 if the access sheath 300 remains. Alternatively, the applicator 416 may be removed from the access sheath 300, and the expandable device 410 may be reintroduced through the access sheath 300, as described above. Upon completing treatment, the applicator 416 and/or access sheath 300 may be removed and the patient treated using known methods for closing the passage 12.

Exemplary embodiments of the present invention are described above. Those skilled in the art will recognize that many embodiments are possible within the scope of the invention. Other variations, modifications, and combinations of the various components and methods described herein can certainly be made and still fall within the scope of the invention. For example, any of the treatment devices described herein may be combined with any of the delivery systems and methods also described herein. Thus, the invention is limited only by the following claims, and equivalents thereto.

We claim:

1. A system for brachytherapy treatment within a body cavity within a patient accessed via a passage through tissue, comprising:
   an access port device comprising a tubular member comprising a proximal end, a distal end sized for introduction through a passage through tissue into a body cavity, and an expandable member comprising a proximal end attached to the tubular member distal end and a distal end extending distally beyond the tubular member distal end, the tubular member further comprising a working channel extending between the tubular member proximal end and the tubular member distal end and communicating with the interior of the expandable member, the expandable member comprising a substantially enclosed interior in communication with the working channel and an inflation lumen extending between the tubular member proximal end and the tubular member distal end and communicating with the interior of the expandable member for delivering inflation media into the interior for expanding the expandable member; and
   an expandable brachytherapy applicator comprising an applicator proximal end, an applicator distal end sized for introduction through the working channel of the access port device into the interior of the expandable member, the applicator comprising a plurality of elongate members extending between the applicator proximal and distal ends and comprising pathways for delivering a source of radiation from the applicator proximal end to a distal portion of the applicator, the elongate members movable from a collapsed configuration to an expanded configuration to expand the applicator distal end within the interior of the expandable member.

2. The system of claim 1, further comprising a source of radiation receivable along the pathways of the applicator elongate members.

3. The system of claim 1, wherein the applicator elongate members comprise catheters comprising lumens extending between the applicator proximal end and the applicator distal end for receiving a source of radiation therein, thereby defining the pathways.

4. The system of claim 1, wherein the access port device further comprises a valve disposed within the working channel adjacent the tubular member proximal end and configured to allow the applicator to be inserted through the working channel into the interior of the expandable member without inflation media within the interior escaping substantially through the working channel.

5. The system of claim 4, wherein the valve comprises one or more duck bill valves in the working channel for substantially preventing fluid flow proximally out of the working channel while accommodating the applicator to be introduced therethrough.

6. The system of claim 1, further comprising a hub on the tubular member proximal end, the hub comprising an index thereon for determining a rotational orientation of the applicator when inserted into the working channel.

7. The system of claim 6, wherein the index comprises a plurality of position labels and a respective plurality of grooves associated with respective position labels.

8. The system of claim 7, wherein the applicator comprises an indexing bushing and a tab, the tab configured to be slidably received in one of the grooves when the applicator is inserted into the working channel to prevent rotational movement of the applicator relative to the access port device.

9. The system of claim 8, wherein the indexing bushing comprises a plurality of catheter labels, the catheter labels matching the position labels on the index.

10. The system of claim 1, wherein the applicator comprises an elongate core member, a distal tip coupled to the elongate core member, and an actuator coupled to the elongate members and axially movable relative to the distal tip for directing the elongate members between the collapsed and expanded configurations.

11. The system of claim 10, wherein the elongate members extend substantially parallel to the elongate core member in the collapsed configuration.

12. The system of claim 11, wherein the elongate members bow radially outwardly in the expanded configuration to form a pear shape that bulges near the distal tip of the elongate core member and tapers towards the actuator.

13. The system of claim 10, wherein the elongate members comprise a pair of elongate members that expand outwardly away from one another substantially within a plane in the expanded configuration.

14. The system of claim 1, wherein the working channel terminates at the proximal end of the expandable member such that, when the applicator is introduced through the working channel, the distal portion is located within the interior of the expandable member beyond the tubular member distal end.

15. The system of claim 1, wherein there are no pathways for receiving a source of radiation on the expandable member such that the elongate members provide a single layer of pathways for receiving a source of radiation.

16. An access port device for accessing a body cavity of a patient via a passage through tissue, comprising:
- a tubular member comprising a proximal end, a distal end sized for introduction through a passage through tissue into a body cavity, and an inflation lumen and a working channel within the tubular member extending between the proximal end and the distal end;
- an expandable member comprising a proximal end attached to the tubular member distal end and a distal end extending distally beyond the tubular member distal end and terminating in a closed distal tip, the expandable member configured for delineating or dilating tissue surrounding a body cavity within which the expandable member is expanded, the expandable member comprising a substantially enclosed interior in communication with the inflation lumen and the working channel; and
- a valve disposed within the working channel adjacent the tubular member proximal end and configured to allow a device to be inserted through the working channel into the interior of the expandable member without inflation media within the interior escaping substantially through the working channel.

17. The access port device of claim 16, wherein the inflation lumen is disposed within the tubular member adjacent the working channel.

18. The access port device of claim 16, wherein the working channel terminates at the proximal end of the expandable member.

19. A system for brachytherapy treatment within a target tissue region within a patient accessed via a passage through tissue, comprising:
- an access sheath comprising a proximal portion, a distal section sized for introduction into a passage through tissue to access a target tissue region, and a bendable intermediate section between the proximal portion and the distal portion, the access sheath comprising a "C" shaped cross-section including longitudinal edges that at least partially define a lumen extending from the proximal portion to the distal portion;
- an expandable device comprising a tubular member including a tubular member proximal end, a tubular member distal end sized for introduction through the lumen of the access sheath, an expandable member comprising a proximal end attached to the tubular member distal end, a distal end extending distally beyond the tubular member distal end, and an inflation lumen extending between the tubular member proximal end and the tubular member distal end that communicates with an interior of the expandable member; and
- an expandable brachytherapy applicator comprising an applicator proximal end, an applicator distal end sized for introduction through the lumen of the access sheath, the expandable brachytherapy applicator comprising a plurality of elongate members extending between the applicator proximal end and applicator distal end and comprising pathways for delivering a source of radiation from the applicator proximal end to a distal portion of the expandable brachytherapy applicator, the distal portion movable from a collapsed configuration to an expanded configuration,
- wherein the longitudinal edges of the access sheath are spaced apart from one another to define a gap extending between the proximal portion and the distal portion of the access sheath, the longitudinal edges being sufficiently flexible to be directed apart from one another to increase a width of the gap to accommodate removing the access sheath from around at least one of the expandable device and the expandable brachytherapy applicator.

20. The system of claim 19, wherein the bendable section of the access sheath is bendable up to an angle of at least about ninety degrees.

21. The system of claim 19, wherein the tubular member further comprises a working channel extending between the tubular member proximal end and the tubular member distal end and communicating with the interior of the expandable member, the working channel comprising a valve to accommodate introducing the applicator through the working channel without substantial leakage of fluid from within the expandable member.

22. The system of claim 19, wherein the tubular member is substantially flexible such that, when the bendable section of the access sheath is bent with the tubular member within the access sheath lumen, the tubular member does not substantially restrict bending of the bendable section.

23. The system of claim 19, wherein the bendable section of the access sheath comprises a plurality of corrugations that accommodate bending of the bendable section.

24. The system of claim 19, wherein the bendable section of the access sheath comprises a plurality of slots that accommodate bending of the bendable section.

25. The system of claim 19, wherein the access sheath has a "C" shaped cross-section that extends from a proximal end of the access sheath through the proximal and distal portions to a distal end of the access sheath.

26. A method for brachytherapy treatment of a target tissue region within a patient's body, comprising:
- introducing a distal portion of an access sheath having a "C" shaped cross-section into a passage through tissue to access a target tissue region such that a proximal portion of the access sheath remains outside the patient's body;
- introducing a distal end of an expandable device through the passage through tissue until a balloon on the distal end is disposed within the target tissue region;
- expanding the balloon to dilate or manipulate tissue within the target tissue region;
- collapsing the balloon;
- withdrawing the expandable device from the target tissue region through the access sheath, leaving the access sheath within the passage through tissue; and
- introducing a distal portion of an applicator through the access sheath into the target tissue region to treat tissue within the target tissue region.

27. The method of claim 26, further comprising bending a proximal portion of the access sheath relative to the distal portion to minimize a profile of the access sheath outside the patient's body.

28. The method of claim 26, wherein the expandable device is inserted into the access sheath before the access sheath is introduced into the passage through tissue, and wherein the access sheath and the expandable device are introduced into the passage through tissue with the expandable device inserted into the access sheath.

29. The method of claim 26, wherein the access sheath is introduced into the passage through tissue before the expandable device, and wherein the expandable device is introduced into the passage through tissue through a lumen of the access sheath.

30. A method for brachytherapy treatment of tissue within a patient's body, comprising:
- introducing a distal end of an access port device into a body cavity;

expanding an expandable member extending beyond the distal end of the access port device within the body cavity;

introducing a distal portion of an applicator through the access port device into the body cavity with the distal portion of the applicator in a collapsed configuration;

directing the distal portion of the applicator to an expanded configuration within the expandable member after expanding the expandable member within the body cavity and introducing the distal portion of the applicator into the body cavity; and deflating the expandable member after directing the distal portion of the applicator to the expanded configuration;

after deflating the expandable member, delivering radiation to a target location adjacent the body cavity via the distal portion of the applicator.

31. The method of claim 30, wherein the body cavity comprises a vaginal cavity.

32. The method of claim 30, further comprising:
directing the distal portion of the applicator to the collapsed configuration; and
withdrawing the applicator from the body cavity while leaving the distal end of the access port device within the body cavity.

33. The method of claim 32, wherein the distal end of the access port device is left within the body cavity for at least twenty four (24) hours.

34. The method of claim 33, further comprising:
advancing a distal portion of a second applicator through the access port device into the body cavity with the distal portion of the second applicator in a collapsed configuration;
directing the distal portion of the second applicator to an expanded configuration within the body cavity; and
delivering radiation to the target location via the distal portion of the second applicator.

* * * * *